United States Patent
Perkins et al.

(10) Patent No.: US 8,845,705 B2
(45) Date of Patent: *Sep. 30, 2014

(54) OPTICAL COCHLEAR STIMULATION DEVICES AND METHODS

(75) Inventors: Rodney C. Perkins, Woodside, CA (US); Sunil Puria, Sunnyvale, CA (US)

(73) Assignee: EarLens Corporation, Redwood City, CA (US)

( * ) Notice: Subject to any disclaimer, the term of this patent is extended or adjusted under 35 U.S.C. 154(b) by 54 days.

This patent is subject to a terminal disclaimer.

(21) Appl. No.: 12/822,810

(22) Filed: Jun. 24, 2010

(65) Prior Publication Data

US 2011/0152976 A1 Jun. 23, 2011

Related U.S. Application Data

(60) Provisional application No. 61/220,122, filed on Jun. 24, 2009.

(51) Int. Cl.
*H04R 25/00* (2006.01)
*A61N 5/06* (2006.01)
*H04R 23/00* (2006.01)
*A61N 1/36* (2006.01)

(52) U.S. Cl.
CPC .......... *A61N 5/0622* (2013.01); *H04R 2225/67* (2013.01); *H04R 23/008* (2013.01); *A61N 1/36032* (2013.01); *H04R 2225/021* (2013.01); *H04R 25/606* (2013.01); *A61N 5/0601* (2013.01); *A61N 2005/063* (2013.01)
USPC .................................. 607/89; 607/92; 600/25

(58) Field of Classification Search
USPC ........................................ 607/88–94; 600/25
See application file for complete search history.

(56) References Cited

U.S. PATENT DOCUMENTS 3,209,082 A 9/1965 McCarrell et al.
3,440,314 A 4/1969 Frisch
(Continued)

FOREIGN PATENT DOCUMENTS

DE 2044870 A1 3/1972
DE 3243850 A1 5/1984
(Continued)

OTHER PUBLICATIONS

International search report dated Mar. 29, 2011 for PCT/US2010/039776.
(Continued)

*Primary Examiner* — Dawayne A Pinkney
(74) *Attorney, Agent, or Firm* — Wilson Sonsini Goodrich & Rosati

(57) ABSTRACT

An output assembly is sized for placement in the middle and inner ear, such that removal of bone can be decreased. The output assembly may comprise at least one photo detector, a demultiplexer and an optical array sized to pass through an incision in the eardrum. An input transducer assembly is configured to transmit a multiplexed optical signal to the output assembly. The input assembly can be configured to transmit the multiplexed optical signal through the eardrum, such that tissue removal can be decreased and the device can be placed without removal of bone, for example. The multiplexed optical signal may comprise a pulse width modulated signal so as to decrease the effect of non-linearities of the light source and light detector and provide quality sound to the user.

80 Claims, 11 Drawing Sheets

(56) References Cited

U.S. PATENT DOCUMENTS

| | | |
|---|---|---|
| 3,549,818 A | 12/1970 | Turner et al. |
| 3,585,416 A | 6/1971 | Mellen |
| 3,594,514 A | 7/1971 | Wingrove |
| 3,710,399 A | 1/1973 | Hurst |
| 3,712,962 A | 1/1973 | Epley |
| 3,764,748 A | 10/1973 | Branch et al. |
| 3,808,179 A | 4/1974 | Gaylord |
| 3,882,285 A | 5/1975 | Nunley et al. |
| 3,985,977 A | 10/1976 | Beaty et al. |
| 4,002,897 A | 1/1977 | Kleinman et al. |
| 4,061,972 A | 12/1977 | Burgess |
| 4,075,042 A | 2/1978 | Das |
| 4,098,277 A | 7/1978 | Mendell |
| 4,109,116 A | 8/1978 | Victoreen |
| 4,120,570 A | 10/1978 | Gaylord |
| 4,248,899 A | 2/1981 | Lyon et al. |
| 4,252,440 A | 2/1981 | Frosch et al. |
| 4,303,772 A | 12/1981 | Novicky |
| 4,319,359 A | 3/1982 | Wolf |
| 4,334,315 A | 6/1982 | Ono et al. |
| 4,334,321 A | 6/1982 | Edelman |
| 4,339,954 A | 7/1982 | Anson et al. |
| 4,357,497 A | 11/1982 | Hochmair et al. |
| 4,380,689 A | 4/1983 | Giannetti |
| 4,428,377 A | 1/1984 | Zollner et al. |
| 4,524,294 A | 6/1985 | Brody |
| 4,540,761 A | 9/1985 | Kawamura et al. |
| 4,556,122 A | 12/1985 | Goode |
| 4,592,087 A | 5/1986 | Killion |
| 4,606,329 A | 8/1986 | Hough |
| 4,611,598 A | 9/1986 | Hortmann et al. |
| 4,628,907 A | 12/1986 | Epley |
| 4,641,377 A | 2/1987 | Rush et al. |
| 4,654,554 A | 3/1987 | Kishi |
| 4,689,819 A | 8/1987 | Killion |
| 4,696,287 A | 9/1987 | Hortmann et al. |
| 4,729,366 A | 3/1988 | Schaefer |
| 4,741,339 A | 5/1988 | Harrison et al. |
| 4,742,499 A | 5/1988 | Butler |
| 4,756,312 A | 7/1988 | Epley |
| 4,766,607 A | 8/1988 | Feldman |
| 4,774,933 A | 10/1988 | Hough et al. |
| 4,776,322 A | 10/1988 | Hough et al. |
| 4,782,818 A | 11/1988 | Mori |
| 4,800,884 A | 1/1989 | Heide et al. |
| 4,800,982 A | 1/1989 | Carlson |
| 4,817,607 A | 4/1989 | Tatge |
| 4,840,178 A | 6/1989 | Heide et al. |
| 4,845,755 A | 7/1989 | Busch et al. |
| 4,865,035 A | 9/1989 | Mori |
| 4,932,405 A | 6/1990 | Peeters et al. |
| 4,936,305 A | 6/1990 | Ashtiani et al. |
| 4,944,301 A | 7/1990 | Widin et al. |
| 4,948,855 A | 8/1990 | Novicky |
| 4,957,478 A | 9/1990 | Maniglia |
| 4,999,819 A | 3/1991 | Newnham et al. |
| 5,003,608 A | 3/1991 | Carlson |
| 5,012,520 A | 4/1991 | Steeger |
| 5,015,224 A | 5/1991 | Mariglia |
| 5,015,225 A | 5/1991 | Hough et al. |
| 5,031,219 A | 7/1991 | Ward et al. |
| 5,061,282 A | 10/1991 | Jacobs |
| 5,066,091 A | 11/1991 | Stoy et al. |
| 5,094,108 A | 3/1992 | Kim et al. |
| 5,117,461 A | 5/1992 | Moseley |
| 5,142,186 A | 8/1992 | Cross et al. |
| 5,163,957 A | 11/1992 | Sade et al. |
| 5,167,235 A | 12/1992 | Seacord et al. |
| 5,201,007 A | 4/1993 | Ward et al. |
| 5,259,032 A | 11/1993 | Perkins et al. |
| 5,272,757 A | 12/1993 | Scofield et al. |
| 5,276,910 A | 1/1994 | Buchele |
| 5,277,694 A | 1/1994 | Leysieffer et al. |
| 5,360,388 A | 11/1994 | Spindel et al. |
| 5,378,933 A | 1/1995 | Pfannenmueller et al. |
| 5,402,496 A | 3/1995 | Soli et al. |
| 5,411,467 A | 5/1995 | Hortmann et al. |
| 5,425,104 A | 6/1995 | Shennib |
| 5,440,082 A | 8/1995 | Claes |
| 5,440,237 A | 8/1995 | Brown et al. |
| 5,455,994 A | 10/1995 | Termeer et al. |
| 5,456,654 A | 10/1995 | Ball |
| 5,531,787 A | 7/1996 | Lesinski et al. |
| 5,531,954 A | 7/1996 | Heide et al. |
| 5,535,282 A | 7/1996 | Luca |
| 5,554,096 A | 9/1996 | Ball |
| 5,558,618 A | 9/1996 | Maniglia |
| 5,571,148 A | 11/1996 | Loeb et al. |
| 5,572,594 A | 11/1996 | Devoe et al. |
| 5,606,621 A | 2/1997 | Reiter et al. |
| 5,624,376 A | 4/1997 | Ball et al. |
| 5,707,338 A | 1/1998 | Adams et al. |
| 5,715,321 A | 2/1998 | Andrea et al. |
| 5,721,783 A | 2/1998 | Anderson |
| 5,722,411 A | 3/1998 | Suzuki et al. |
| 5,729,077 A | 3/1998 | Newnham et al. |
| 5,740,258 A | 4/1998 | Goodwin-Johansson |
| 5,749,912 A | 5/1998 | Zhang et al. |
| 5,762,583 A | 6/1998 | Adams et al. |
| 5,772,575 A | 6/1998 | Lesinski et al. |
| 5,774,259 A | 6/1998 | Saitoh et al. |
| 5,782,744 A | 7/1998 | Money |
| 5,788,711 A | 8/1998 | Lehner et al. |
| 5,795,287 A | 8/1998 | Ball et al. |
| 5,797,834 A | 8/1998 | Goode |
| 5,800,336 A | 9/1998 | Ball et al. |
| 5,804,109 A | 9/1998 | Perkins |
| 5,804,907 A | 9/1998 | Park et al. |
| 5,814,095 A | 9/1998 | Muller et al. |
| 5,824,022 A | 10/1998 | Zilberman et al. |
| 5,825,122 A | 10/1998 | Givargizov et al. |
| 5,836,863 A | 11/1998 | Bushek et al. |
| 5,842,967 A | 12/1998 | Kroll |
| 5,857,958 A | 1/1999 | Ball et al. |
| 5,859,916 A | 1/1999 | Ball et al. |
| 5,879,283 A | 3/1999 | Adams et al. |
| 5,888,187 A | 3/1999 | Jaeger et al. |
| 5,897,486 A | 4/1999 | Ball et al. |
| 5,899,847 A | 5/1999 | Adams et al. |
| 5,900,274 A | 5/1999 | Chatterjee et al. |
| 5,906,635 A | 5/1999 | Maniglia |
| 5,913,815 A | 6/1999 | Ball et al. |
| 5,922,017 A | 7/1999 | Bredberg et al. |
| 5,940,519 A | 8/1999 | Kuo |
| 5,949,895 A | 9/1999 | Ball et al. |
| 5,984,859 A | 11/1999 | Lesinski |
| 5,987,146 A | 11/1999 | Pluvinage et al. |
| 6,005,955 A | 12/1999 | Kroll et al. |
| 6,024,717 A | 2/2000 | Ball et al. |
| 6,038,480 A * | 3/2000 | Hrdlicka et al. ............... 607/116 |
| 6,045,528 A | 4/2000 | Arenberg et al. |
| 6,050,933 A | 4/2000 | Bushek et al. |
| 6,068,589 A | 5/2000 | Neukermans |
| 6,068,590 A | 5/2000 | Brisken |
| 6,084,975 A | 7/2000 | Perkins et al. |
| 6,093,144 A | 7/2000 | Jaeger et al. |
| 6,137,889 A | 10/2000 | Shennib et al. |
| 6,139,488 A | 10/2000 | Ball |
| 6,153,966 A | 11/2000 | Neukermans |
| 6,174,278 B1 | 1/2001 | Jaeger et al. |
| 6,181,801 B1 | 1/2001 | Puthuff et al. |
| 6,190,305 B1 | 2/2001 | Ball et al. |
| 6,190,306 B1 | 2/2001 | Kennedy |
| 6,208,445 B1 | 3/2001 | Reime |
| 6,216,040 B1 | 4/2001 | Harrison |
| 6,217,508 B1 | 4/2001 | Ball et al. |
| 6,222,302 B1 | 4/2001 | Imade et al. |
| 6,222,927 B1 | 4/2001 | Feng et al. |
| 6,240,192 B1 | 5/2001 | Brennan et al. |
| 6,241,767 B1 | 6/2001 | Stennert et al. |
| 6,261,224 B1 | 7/2001 | Adams et al. |
| 6,277,148 B1 | 8/2001 | Dormer |
| 6,312,959 B1 | 11/2001 | Datskos |
| 6,339,648 B1 | 1/2002 | McIntosh et al. |

(56) References Cited

U.S. PATENT DOCUMENTS

| | | | |
|---|---|---|---|
| 6,342,035 B1 * | 1/2002 | Kroll et al. | 600/25 |
| 6,354,990 B1 | 3/2002 | Juneau et al. | |
| 6,366,863 B1 | 4/2002 | Bye et al. | |
| 6,374,143 B1 | 4/2002 | Berrang et al. | |
| 6,385,363 B1 | 5/2002 | Rajic et al. | |
| 6,387,039 B1 | 5/2002 | Moses | |
| 6,390,971 B1 | 5/2002 | Adams et al. | |
| 6,393,130 B1 | 5/2002 | Stonikas et al. | |
| 6,422,991 B1 | 7/2002 | Jaeger | |
| 6,432,248 B1 | 8/2002 | Popp et al. | |
| 6,436,028 B1 | 8/2002 | Dormer | |
| 6,438,244 B1 | 8/2002 | Juneau et al. | |
| 6,445,799 B1 | 9/2002 | Taenzer et al. | |
| 6,473,512 B1 | 10/2002 | Juneau et al. | |
| 6,475,134 B1 | 11/2002 | Ball et al. | |
| 6,491,644 B1 | 12/2002 | Vujanic et al. | |
| 6,493,453 B1 | 12/2002 | Glendon | |
| 6,493,454 B1 | 12/2002 | Loi et al. | |
| 6,498,858 B2 | 12/2002 | Kates | |
| 6,507,758 B1 | 1/2003 | Greenberg et al. | |
| 6,519,376 B2 | 2/2003 | Biagi et al. | |
| 6,536,530 B2 | 3/2003 | Schultz et al. | |
| 6,537,200 B2 | 3/2003 | Leysieffer et al. | |
| 6,549,633 B1 | 4/2003 | Westermann | |
| 6,554,761 B1 | 4/2003 | Puria et al. | |
| 6,575,894 B2 | 6/2003 | Leysieffer et al. | |
| 6,592,513 B1 | 7/2003 | Kroll et al. | |
| 6,603,860 B1 | 8/2003 | Taenzer et al. | |
| 6,620,110 B2 | 9/2003 | Schmid | |
| 6,626,822 B1 | 9/2003 | Jaeger et al. | |
| 6,629,922 B1 | 10/2003 | Puria et al. | |
| 6,668,062 B1 | 12/2003 | Luo et al. | |
| 6,676,592 B2 | 1/2004 | Ball et al. | |
| 6,695,943 B2 | 2/2004 | Juneau et al. | |
| 6,724,902 B1 | 4/2004 | Shennib et al. | |
| 6,728,024 B2 | 4/2004 | Ribak | |
| 6,735,318 B2 | 5/2004 | Cho | |
| 6,754,358 B1 | 6/2004 | Boeson et al. | |
| 6,754,537 B1 | 6/2004 | Harrison et al. | |
| 6,801,629 B2 | 10/2004 | Brimhall et al. | |
| 6,829,363 B2 | 12/2004 | Sacha | |
| 6,842,647 B1 | 1/2005 | Griffith et al. | |
| 6,888,949 B1 | 5/2005 | Vanden Berghe et al. | |
| 6,900,926 B2 | 5/2005 | Ribak | |
| 6,912,289 B2 | 6/2005 | Vonlanthen et al. | |
| 6,920,340 B2 | 7/2005 | Laderman | |
| 6,940,989 B1 | 9/2005 | Shennib et al. | |
| D512,979 S | 12/2005 | Corcoran et al. | |
| 6,975,402 B2 | 12/2005 | Bisson et al. | |
| 6,978,159 B2 | 12/2005 | Feng et al. | |
| 7,043,037 B2 | 5/2006 | Lichtblau | |
| 7,050,675 B2 | 5/2006 | Zhou | |
| 7,057,256 B2 | 6/2006 | Carey, III et al. | |
| 7,058,182 B2 | 6/2006 | Kates | |
| 7,072,475 B1 | 7/2006 | DeNap et al. | |
| 7,076,076 B2 | 7/2006 | Bauman | |
| 7,095,981 B1 | 8/2006 | Voroba et al. | |
| 7,167,572 B1 | 1/2007 | Harrison et al. | |
| 7,174,026 B2 | 2/2007 | Niederdrank | |
| 7,203,331 B2 | 4/2007 | Boesen | |
| 7,239,069 B2 | 7/2007 | Cho | |
| 7,245,732 B2 | 7/2007 | Jorgensen et al. | |
| 7,255,457 B2 | 8/2007 | Ducharme et al. | |
| 7,289,639 B2 | 10/2007 | Abel et al. | |
| 7,322,930 B2 | 1/2008 | Jaeger et al. | |
| 7,349,741 B2 | 3/2008 | Maltan et al. | |
| 7,354,792 B2 | 4/2008 | Carey, III et al. | |
| 7,376,563 B2 | 5/2008 | Leysieffer et al. | |
| 7,390,689 B2 | 6/2008 | Mazur et al. | |
| 7,394,909 B1 | 7/2008 | Widmer et al. | |
| 7,421,087 B2 | 9/2008 | Perkins et al. | |
| 7,424,122 B2 | 9/2008 | Ryan | |
| 7,444,877 B2 | 11/2008 | Li et al. | |
| 7,547,275 B2 | 6/2009 | Cho | |
| 7,645,877 B2 | 1/2010 | Gmeiner et al. | |
| 7,668,325 B2 | 2/2010 | Puria et al. | |
| 2001/0003788 A1 | 6/2001 | Ball et al. | |
| 2001/0027342 A1 | 10/2001 | Dormer | |
| 2001/0043708 A1 | 11/2001 | Brimhall | |
| 2001/0053871 A1 | 12/2001 | Zilberman et al. | |
| 2002/0012438 A1 | 1/2002 | Leysieffer et al. | |
| 2002/0029070 A1 | 3/2002 | Leysieffer et al. | |
| 2002/0030871 A1 | 3/2002 | Anderson et al. | |
| 2002/0035309 A1 | 3/2002 | Leysieffer | |
| 2002/0086715 A1 | 7/2002 | Sahagen | |
| 2002/0172350 A1 | 11/2002 | Edwards et al. | |
| 2002/0183587 A1 | 12/2002 | Dormer | |
| 2003/0064746 A1 | 4/2003 | Rader et al. | |
| 2003/0097178 A1 | 5/2003 | Roberson et al. | |
| 2003/0125602 A1 | 7/2003 | Sokolich et al. | |
| 2003/0142841 A1 | 7/2003 | Wiegand | |
| 2003/0208099 A1 | 11/2003 | Ball | |
| 2004/0165742 A1 | 8/2004 | Shennib et al. | |
| 2004/0184732 A1 | 9/2004 | Zhou | |
| 2004/0208333 A1 | 10/2004 | Cheung et al. | |
| 2004/0234089 A1 | 11/2004 | Rembrand et al. | |
| 2004/0234092 A1 | 11/2004 | Wada et al. | |
| 2004/0240691 A1 | 12/2004 | Grafenberg | |
| 2005/0020873 A1 | 1/2005 | Berrang et al. | |
| 2005/0036639 A1 | 2/2005 | Bachler et al. | |
| 2005/0163333 A1 | 7/2005 | Abel et al. | |
| 2005/0226446 A1 | 10/2005 | Luo et al. | |
| 2006/0023908 A1 | 2/2006 | Perkins et al. | |
| 2006/0058573 A1 | 3/2006 | Neisz et al. | |
| 2006/0062420 A1 | 3/2006 | Araki | |
| 2006/0107744 A1 | 5/2006 | Li et al. | |
| 2006/0129210 A1 | 6/2006 | Cantin et al. | |
| 2006/0161255 A1 | 7/2006 | Zarowski et al. | |
| 2006/0177079 A1 | 8/2006 | Baekgaard Jensen et al. | |
| 2006/0183965 A1 | 8/2006 | Kasic, II et al. | |
| 2006/0189841 A1 | 8/2006 | Pluvinage | |
| 2006/0231914 A1 | 10/2006 | Carey, III et al. | |
| 2006/0233398 A1 | 10/2006 | Husung | |
| 2007/0083078 A1 | 4/2007 | Easter et al. | |
| 2007/0100197 A1 | 5/2007 | Perkins et al. | |
| 2007/0127748 A1 | 6/2007 | Carlile et al. | |
| 2007/0135870 A1 | 6/2007 | Shanks et al. | |
| 2007/0161848 A1 | 7/2007 | Dalton et al. | |
| 2007/0191673 A1 | 8/2007 | Ball et al. | |
| 2007/0225776 A1 | 9/2007 | Fritsch et al. | |
| 2007/0236704 A1 | 10/2007 | Carr | |
| 2007/0250119 A1 | 10/2007 | Tyler et al. | |
| 2007/0251082 A1 | 11/2007 | Milojevic et al. | |
| 2007/0286429 A1 | 12/2007 | Grafenberg et al. | |
| 2008/0021518 A1 | 1/2008 | Hochmair et al. | |
| 2008/0051623 A1 | 2/2008 | Schneider et al. | |
| 2008/0107292 A1 | 5/2008 | Kornagel | |
| 2008/0188707 A1 | 8/2008 | Bernard et al. | |
| 2008/0298600 A1 | 12/2008 | Poe et al. | |
| 2009/0023976 A1 | 1/2009 | Cho et al. | |
| 2009/0043149 A1 | 2/2009 | Abel et al. | |
| 2009/0092271 A1 | 4/2009 | Fay et al. | |
| 2009/0097681 A1 | 4/2009 | Puria et al. | |
| 2009/0141919 A1 | 6/2009 | Spitaels et al. | |
| 2010/0034409 A1 | 2/2010 | Fay et al. | |
| 2010/0048982 A1 | 2/2010 | Puria et al. | |
| 2010/0114190 A1 * | 5/2010 | Bendett et al. | 607/3 |
| 2010/0312040 A1 | 12/2010 | Puria et al. | |
| 2010/0317914 A1 | 12/2010 | Puria et al. | |
| 2011/0144719 A1 | 6/2011 | Perkins et al. | |

FOREIGN PATENT DOCUMENTS

| | | |
|---|---|---|
| DE | 3508830 A1 | 9/1986 |
| EP | 0242038 A3 | 5/1987 |
| EP | 0242038 A2 | 10/1987 |
| EP | 0291325 A2 | 11/1988 |
| EP | 0296092 A2 | 12/1988 |
| EP | 0296092 A3 | 8/1989 |
| EP | 0352954 A2 | 1/1990 |
| EP | 0291325 A3 | 6/1990 |
| EP | 0352954 A3 | 8/1991 |
| EP | 1845919 A1 | 10/2007 |
| EP | 2272520 A1 | 1/2011 |

(56) References Cited

FOREIGN PATENT DOCUMENTS

| | | |
|---|---|---|
| FR | 2455820 A1 | 11/1980 |
| JP | 60-154800 A | 8/1985 |
| JP | 64-43252 A | 2/1989 |
| JP | 09-327098 A | 12/1997 |
| JP | 2006-060833 A | 3/2006 |
| KR | 10-0624445 B1 | 9/2006 |
| WO | WO 92/09181 A1 | 5/1992 |
| WO | WO 97/36457 A1 | 10/1997 |
| WO | WO 97/45074 A1 | 12/1997 |
| WO | WO 98/06236 A1 | 2/1998 |
| WO | WO 99/03146 A1 | 1/1999 |
| WO | WO 99/15111 A1 | 4/1999 |
| WO | WO 01/50815 A1 | 7/2001 |
| WO | WO 01/58206 A2 | 8/2001 |
| WO | WO 01/58206 A3 | 2/2002 |
| WO | WO 02/39874 A2 | 5/2002 |
| WO | WO 02/39874 A3 | 2/2003 |
| WO | WO 03/063542 A2 | 7/2003 |
| WO | WO 03/063542 A3 | 1/2004 |
| WO | WO 2004/010733 A1 | 1/2004 |
| WO | WO 2005/015952 A1 | 2/2005 |
| WO | WO 2006/039146 A2 | 4/2006 |
| WO | WO 2006/042298 A2 | 4/2006 |
| WO | WO 2006/075169 A1 | 7/2006 |
| WO | WO 2006/075175 A1 | 7/2006 |
| WO | WO 2006/042298 A3 | 10/2006 |
| WO | WO 2009/047370 A2 | 4/2009 |
| WO | WO 2009/056167 A1 | 5/2009 |
| WO | WO 2009/062142 A1 | 5/2009 |
| WO | WO 2009/047370 A3 | 7/2009 |
| WO | WO 2009/125903 A1 | 10/2009 |

OTHER PUBLICATIONS

U.S. Appl. No. 60/702,532, filed Jul. 25, 2005, Aljuri.
U.S. Appl. No. 61/099,087, filed Sep. 22, 2008, Rucker.
Atasoy [Paper] Opto-acoustic Imaging. For BYM504E Biomedical Imaging Systems class at ITU, downloaded from the Internet www2.itu.edu.td—cilesiz/courses/BYM504-2005-OA 504041413.pdf, 14 pages.
Athanassiou, et al. Laser controlled photomechanical actuation of photochromic polymers Microsystems. Rev. Adv. Mater. Sci. 2003; 5:245-251.
Ayatollahi, et al. Design and Modeling of Micromachined Condenser MEMS Loudspeaker using Permanent Magnet Neodymium-Iron-Boron (Nd—Fe—B). IEEE International Conference on Semiconductor Electronics, 2006. ICSE '06, Oct. 29, 2006-Dec. 1, 2006; 160-166.
Baer, et al. Effects of Low Pass Filtering on the Intelligibility of Speech in Noise for People With and Without Dead Regions at High Frequencies. J. Acost. Soc. Am 112 (3), pt. 1, (Sep. 2002), pp. 1133-1144.
Best, et al. The influence of high frequencies on speech localization. Abstract 981 (Feb. 24, 2003) from www.aro.org/abstracts/abstracts.html.
Birch, et al. Microengineered systems for the hearing impaired. IEE Colloquium on Medical Applications of Microengineering, Jan. 31, 1996; pp. 2/1-2/5.
Burkhard, et al. Anthropometric Manikin for Acoustic Research. J. Acoust. Soc. Am., vol. 58, No. 1, (Jul. 1975), pp. 214-222.
Camacho-Lopez, et al. Fast Liquid Crystal Elastomer Swims Into the Dark, Electronic Liquid Crystal Communications. Nov. 26, 2003; 9 pages total.
Carlile, et al. Spatialisation of talkers and the segregation of concurrent speech. Abstract 1264 (Feb. 24, 2004) from www.aro.org/abstracts/abstracts.html.
Cheng, et al. A Silicon Microspeaker for Hearing Instruments. Journal of Micromechanics and Microengineering 2004; 14(7):859-866.
Datskos, et al. Photoinduced and thermal stress in silicon microcantilevers. Applied Physics Letters. Oct. 19, 1998; 73(16):2319-2321.

Decraemer, et al. A method for determining three-dimensional vibration in the ear. Hearing Res., 77:19-37 (1994).
EAR. Retrieved from the Internet: http://wwwmgs.bionet.nsc.ru/mgs/gnw/trrd/thesaurus/Se/ear.html. Accessed Jun. 17, 2008.
Fay, et al. Cat eardrum response mechanics. Calladine Festschrift (2002), Ed. S. Pellegrino, The Netherlands, Kluwer Academic Publishers.
Fay. Cat eardrum mechanics. Ph.D. thesis. Dissertation submitted to Department of Aeronautics and Astronautics. Standford University. May 2001; 210 pages total.
Fletcher. Effects of Distortion on the Individual Speech Sounds. Chapter 18, ASA Edition of Speech and Hearing in Communication, Acoust Soc.of Am. (republished in 1995) pp. 415-423.
Freyman, et al. Spatial Release from Informational Masking in Speech Recognition. J. Acost. Soc. Am., vol. 109, No. 5, pt. 1, (May 2001); 2112-2122.
Freyman, et al. The Role of Perceived Spatial Separation in the Unmasking of Speech. J. Acoust. Soc. Am., vol. 106, No. 6, (Dec. 1999); 3578-3588.
Gennum, GA3280 Preliminary Data Sheet: Voyageur TD Open Platform DSP System for Ultra Low Audio Processing, downloaded from the Internet: www.sounddesigntechnologies.com/products/pdf/37601DOC.pdf, Oct. 2006; 17 pages.
Gobin, et al. Comments on the physical basis of the active materials concept. Proc. SPIE 2003; 4512:84-92.
Hato, et al. Three-dimensional stapes footplate motion in human temporal bones. Audiol. Neurootol., 8:140-152 (Jan. 30, 2003).
Headphones. Wikipedia Entry, downloaded from the Internet: http://en.wikipedia.org/wiki/Headphones. Accessed Oct. 27, 2008.
Hofman, et al. Relearning Sound Localization With New Ears. Nature Neuroscience, vol. 1, No. 5, (Sep. 1998); 417-421.
International search report and written opinion dated Sep. 28, 2010 for PCT/US2010/039209.
Izzo, et al. Laser Stimulation of Auditory Neurons: Effect of Shorter Pulse Duration and Penetration Depth. Biophys J. Apr. 15, 2008;94(8):3159-3166.
Izzo, et al. Laser Stimulation of the Auditory Nerve. Lasers Surg Med. Sep. 2006;38(8):745-753.
Izzo, et al. Selectivity of Neural Stimulation in the Auditory System: A Comparison of Optic and Electric Stimuli. J Biomed Opt. Mar.-Apr. 2007;12(2):021008.
Jin, et al. Speech Localization. J. Audio Eng. Soc. convention paper, presented at the AES 112th Convention, Munich, Germany, May 10-13, 2002, 13 pages total.
Killion. Myths About Hearing Noise and Directional Microphones. The Hearing Review. Feb. 2004; 11(2):14, 16, 18, 19, 72 & 73.
Killion. SNR loss: I can hear what people say but I can't understand them. The Hearing Review, 1997; 4(12):8-14.
Lee, et al. A Novel Opto-Electromagnetic Actuator Coupled to the tympanic Membrane. Journal of Biomechanics. 41(16): 3515-3518.
Lee, et al. The optimal magnetic force for a novel actuator coupled to the tympanic membrane: a finite element analysis. Biomedical engineering: applications, basis and communications. 2007; 19(3):171-177.
Lezal. Chalcogenide glasses—survey and progress. J. Optoelectron Adv Mater., Mar. 2003; 5 (1):23-34.
Markoff. Intuition + Money: An Aha Moment. New York Times Oct. 11, 2008, p. BU4, 3 pages total.
Martin, et al. Utility of Monaural Spectral Cues is Enhanced in the Presence of Cues to Sound-Source Lateral Angle. JARO. 2004; 5:80-89.
Moore. Loudness perception and intensity resolution. Cochlear Hearing Loss, Chapter 4, pp. 90-115, Whurr Publishers Ltd., London (1998).
Murugasu, et al. Malleus-to-footplate versus malleus-to-stapes-head ossicular reconstruction prostheses: temporal bone pressure gain measurements and clinical audiological data. Otol Neurotol. Jul. 2005; 2694):572-582.
Musicant, et al. Direction-Dependent Spectral Properties of Cat External Ear: New Data and Cross-Species Comparisons. J. Acostic. Soc. Am, May 10-13, 2002, vol. 87, No. 2, (Feb. 1990), pp. 757-781.

(56) References Cited

OTHER PUBLICATIONS

National Semiconductor, LM4673 Boomer: Filterless, 2.65W, Mono, Class D Audio Power Amplifier, [Data Sheet] downloaded from the Internet: <<http://www.national.com/ds/LM/LM4673.pdf>>; Nov. 1, 2007; 24 pages.
O'Connor, et al. Middle ear Cavity and Ear Canal Pressure-Driven Stapes Velocity Responses in Human Cadaveric Temporal Bones. J Acoust Soc Am. Sep. 2006;120(3):1517-28.
Office action dated Oct. 23, 2012 for U.S. Appl. No. 12/818,434.
Perkins, et al. The EarLens System: New sound transduction methods. Hear Res. Feb. 2, 2010; 10 pages total.
Poosanaas, et al. Influence of sample thickness on the performance of photostrictive ceramics, J. App. Phys. Aug. 1, 1998; 84(3):1508-1512.
Puria et al. A gear in the middle ear. ARO Denver CO, 2007b.
Puria, et al. Malleus-to-footplate ossicular reconstruction prosthesis positioning: cochleovestibular pressure optimization. Otol Nerotol. May 2005; 2693):368-379.
Puria, et al. Measurements and model of the cat middle ear: Evidence of tympanic membrane acoustic delay. J. Acoust. Soc. Am., 104(6):3463-3481 (Dec. 1998).
Puria, et al. Middle Ear Morphometry From Cadaveric Temporal Bone MicroCT Imaging. Proceedings of the 4th International Symposium, Zurich, Switzerland, Jul. 27-30, 2006, Middle Ear Mechanics in Research and Otology, pp. 259-268.
Puria, et al. Sound-Pressure Measurements in The Cochlear Vestibule of Human-Cadaver Ears. Journal of the Acoustical Society of America. 1997; 101 (5-1): 2754-2770.
Roush. SiOnyx Brings "Black Silicon" into the Light; Material Could Upend Solar, Imaging Industries. Xconomy, Oct. 12, 2008, retrieved from the Internet: www.xconomy.com/boston/2008/10/12/sionyx-brings-black-silicon-into-the-light¬ material-could-upend-solar-imaging-industries> 4 pages total.
Rubinstein. How Cochlear Implants Encode Speech, Curr Opin Otolaryngol Head Neck Surg. Oct. 2004;12(5):444-8; retrieved from the Internet: www.ohsu.edu/nod/documents/week3/Rubenstein.pdf.
Sekaric, et al. Nanomechanical resonant structures as tunable passive modulators. App. Phys. Lett. Nov. 2003; 80(19):3617-3619.
Shaw. Transformation of Sound Pressure Level From the Free Field to the Eardrum in the Horizontal Plane. J. Acoust. Soc. Am., vol. 56, No. 6, (Dec. 1974), 1848-1861.
Shih. Shape and displacement control of beams with various boundary conditions via photostrictive optical actuators. Proc. IMECE. Nov. 2003; 1-10.
Sound Design Technologies,—Voyager TDTM Open Platform DSP System for Ultra Low Power Audio Processing—GA3280 Data Sheet. Oct. 2007; retrieved from the Internet: www.sounddes.com/pdf/37601DOC.pdf, 15 page total.
Stenfelt, et al. Bone-Conducted Sound: Physiological and Clinical Aspects. Otology & Neurotology, Nov. 2005; 26 (6):1245-1261.
Stuchlik, et al. Micro-Nano Actuators Driven by Polarized Light. IEEE Proc. Sci. Meas. Techn. Mar. 2004; 151(2):131-136.
Suski, et al. Optically activated ZnO/Si02/Si cantilever beams. Sensors and Actuators A (Physical), 0 (nr: 24). 2003; 221-225.
Takagi, et al. Mechanochemical Synthesis of Piezoelectric PLZT Powder. KONA. 2003; 51(21):234-241.
Thakoor, et al. Optical microactuation in piezoceramics. Proc. SPIE. Jul. 1998; 3328:376-391.
Tzou, et al. Smart Materials, Precision Sensors/Actuators, Smart Structures, and Structronic Systems. Mechanics of Advanced Materials and Structures. 2004; 11:367-393.
Uchino, et al. Photostricitve actuators. Ferroelectrics. 2001; 258:147-158.
Vickers, et al. Effects of Low-Pass Filtering on the Intelligibility of Speech in Quiet for People With and Without Dead Regions at High Frequencies. J. Acoust. Soc. Am. Aug. 2001; 110(2):1164-1175.
Vinikman-Pinhasi, et al. Piezoelectric and Piezooptic Effects in Porous Silicon. Applied Physics Letters, Mar. 2006; 88(11): 11905-111906.
Wang, et al. Preliminary assessment of remote photoelectric excitation of an actuator for a hearing omplant. Proceeding of the 2005 IEEE, Engineering in Medicine and Biology 27th annual conference, Shanghai, China. Sep. 1-4, 2005; 6233-6234.
Wiener, et al. On the Sound Pressure Transformation by the Head and Auditory Meatus of the Cat. Acta Otolaryngol. Mar. 2006; 61(3):255-269.
Wightman, et al. Monaural Sound Localization Revisited. J. Acoust. Soc. Am. Feb. 1997; 101(2):1050-1063.
Yu et al. Piezoelectric Microspeaker with Compressive Nitride Diaphragm. The Fifteenth IEEE International Conference on Micro Electro Mechanical Systems, 2002; 260-263.
Yu, et al. Photomechanics: Directed bending of a polymer film by light. Nature. Sep. 2003; 425:145.

* cited by examiner

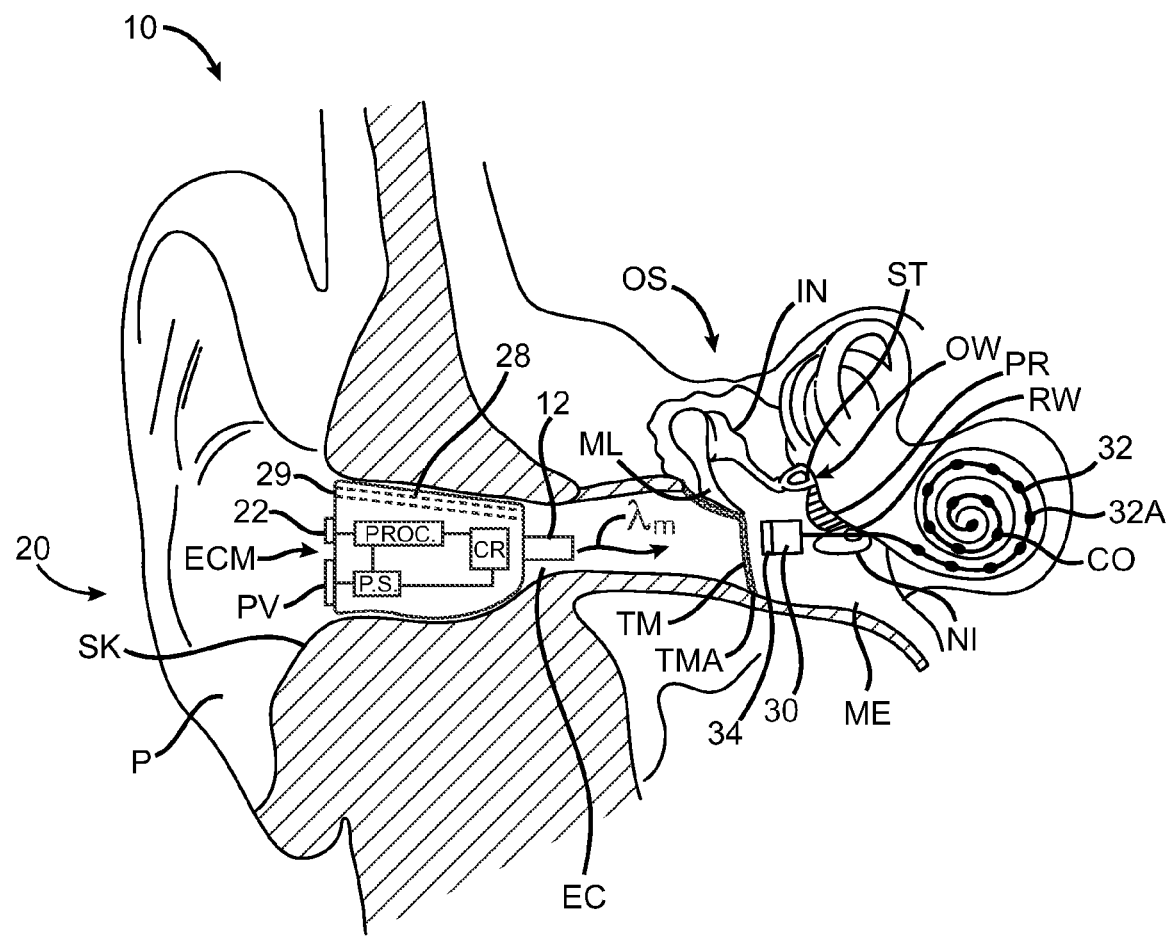
FIG. 1A1

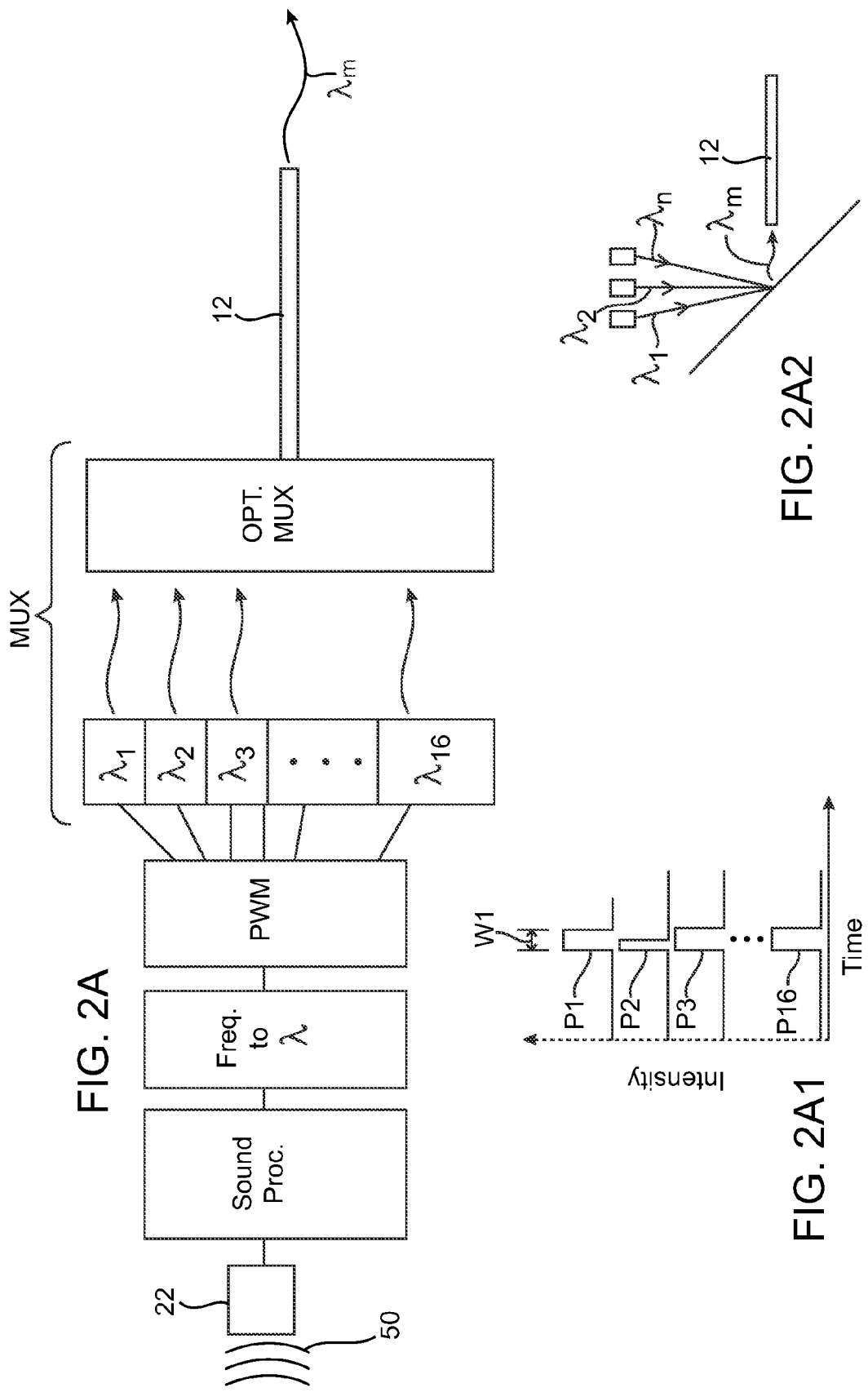

OPTICAL COCHLEAR STIMULATION DEVICES AND METHODS

CROSS-REFERENCES TO RELATED APPLICATIONS

The present patent application is non-provisional and claims priority to U.S. App. Ser. No. 61/220,122 filed 24 Jun. 2009, entitled "Optical Cochlear Stimulation Devices and Methods", the full disclosure of which is incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

Field of the Invention

The present invention relates to tissue stimulation with light generally, and more specifically to stimulation of the cochlea for hearing. Although specific reference is made to cochlear implants, embodiments of the present invention can be used in many applications wherein tissue is stimulated, for example with stimulation of muscles, nerves and neural tissue, for example stimulation of the brain for the treatment of Parkinson's.

The prior devices used to stimulate tissue can be somewhat invasive, in at least some instances. At least some of the prior devices used with cochlear implants can be more invasive than would be ideal. For example, with at least some of the prior cochlear implants bone can be removed in at least some instances. Also, the circuitry associated with cochlear implants can be somewhat larger than ideal. The circuitry coupled to electrodes to stimulate tissue can be somewhat larger than would be ideal for implantation in at least some instances. For example, the circuitry of at least some cochlear electrode array implants may provide current pulses, and the circuitry associated with the current pulses can be larger than would be ideal in at least some instances. Also, packaging of the wires coupled to electrodes and associated insulating materials can be somewhat larger than would be ideal to fit within the cochlea in at least some instances.

With prior cochlear implants, energy can be transmitted through a pair of transmitter and receiver RF coils. A pair of magnets may be used to align the RF coils. One of the two magnets can be semi-permanently implanted in temporal bones in at least some instances. Body implanted magnets are contraindications for MRI machinates, and thus the magnets can be surgically removed prior to imaging in at least some instances. Cochlear implants can be implanted in children as young as 18 months and implanted in adults, and at some point in a person's life, he or she will likely need an MRI in at least some instances. This use of surgically implanted magnets can result in a surgical procedure for magnet removal prior to a MRI and a second procedure for reimplantation in at least some instances.

In at least some instances, implantation of prior cochlear implants includes surgery to the mastoid bone, for example cutting or drilling. The cutting or drilling to the mastoid bone can increase recovery time of the patient and can be somewhat invasive in at least some instances.

Stimulation of tissue with electrical current can be somewhat indirect and may stimulate neural tissue with less specificity than would be ideal in at least some instances, and at least some of the prior cochlear implants may produce a perceived sound quality that is less than ideal in at least some instances. For example, in at least some instances speech recognition may be less than ideal. Also, in at least some instances the prior cochlear implant devices may not provide sound localization cues that are present with natural hearing.

It would be helpful to provide systems, methods and devices to stimulate tissue such as the cochlea in a manner that overcomes at least some of the shortcomings of the prior devices. Ideally such systems, methods and devices of tissue stimulation could be used to stimulate the tissue in a manner that is less invasive, suitable for long term implantation, and provides improved sound quality and improved speech recognition, for example.

BRIEF SUMMARY OF THE INVENTION

The present invention relates to tissue stimulation with light generally, and more specifically to stimulation of the cochlea for hearing. Although specific reference is made to cochlear implants, embodiments of the present invention can be used in many applications wherein tissue is stimulated, for example with stimulation of muscles, nerves and neural tissue, for example the treatment of Parkinson's.

Embodiments of the present invention provide devices, systems and methods of stimulating tissue with light that overcome at least some of the problems associated with the prior devices. Embodiments can be used for cochlear implants and inserted into the cochlea through an incision in the eardrum in a less invasive manner, for example without surgery to the mastoid bone, which can shorten recovery time and make the surgery available to more people. Also, the less invasive surgery without cutting to the mastoid bone can be especially beneficial in small children, for example. A multiplexed signal and power can be transmitted to from an input assembly to an output assembly. The output assembly may comprise at least one waveguide and a plurality of openings to emit light, such that the tissue can be stimulated with the light energy, for example directly or indirectly with the light energy. The optical tissue stimulation can provide improved spatial selectivity, and can be more selective spatially than electrical stimulation, so as to provide improved sound perception. The improve spatial selectivity of the simulation of the cochlear tissue can provide improved sound quality, for example with improved resolution of sound frequencies by the patient. The base band audio signal can be decomposed into a plurality of bandpass filtered channels and a high frequency pulse width modulated signal for each channel can be determined so as to preserve the amplitude and phase of the base band audio signal. With high frequencies stimulation above about 10 kHz, for example above about 20 kHz, the cochlea can low pass filter and demodulate the high frequency pulse width modulated signal into the base band audio sound signal with the amplitude and phase substantially maintained such that the patient can hear the sound with amplitude and phase of the base band audio signal.

The tissue may be stimulated optically in many ways. For example, the cochlear neural tissue may be stimulated with direct tissue absorbance of the light energy to induce stimulation, and the cochlear neural tissue may be stimulated acoustically with light energy absorption of fluid of the cochlea, for example with infrared light. The at least one waveguide may comprise a plurality of distal openings configured for placement in the cochlea to stimulate the cochlea with light energy such that the user perceives sound with improved clarity. The emitted light energy can be localized to portions of the cochlea, and the cross section of the optical fibers can be sized such that many fibers can fit inside the cochlea. For example at least sixteen fibers, (e.g. thirty two fibers or more) can be fit through the round window into the cochlea to stimulate neural tissue at locations of the cochlea. Alternatively, the at least one waveguide may comprise an optical fiber configured to emit light at locations along the fiber in response to mode structure of a laser light source. The output assembly can be sized for placement in the middle and inner ear, such that removal of bone may be decreased. Also, the output assembly may comprise substantially non-magnetic materials such that a person may undergo MRI imaging when the output assembly is implanted. The output assembly may comprise at least one waveguide, a demultiplexer and an optical array sized to pass through an incision in the eardrum. An input transducer assembly can be configured to transmit a multiplexed optical signal to the output assembly. For example, the input assembly can be configured to transmit the multiplexed optical signal through the eardrum such that tissue removal can be decreased and the device may be implanted without removal of bone. The multiplexed optical signal may comprise a pulse width modulated signal so as to decrease the effect of non-linearities of the light source, the waveguide optics and the light detector and provide quality sound to the user.

In a first aspect, embodiments of the present invention provide a method of stimulating tissue. A multiplexed light energy is transmitted to the tissue to stimulate the tissue with the multiplexed light energy.

In an other aspect, embodiments of the present invention provide a method of transmitting a sound to a user, in which the user has a cochlea comprising a tissue. A multiplexed optical signal is transmitted to the tissue of the cochlea such that the user hears the sound in response to the multiplexed optical signal.

In many embodiments, the multiplexed optical signal is transmitted through an eardrum and can be transmitted through the eardrum in many ways. The multiplexed optical signal can be transmitted to an optical structure supported with the middle ear, in which the optical structure is configured to separate wavelengths of the multiplexed signal to stimulate the cochlea. The optical structure can be affixed to the middle ear, and can be sized to pass through an incision in the eardrum for placement in the middle ear. The optical structure may comprise at least one of an optical filter, an optical fiber, a grating, an etalon, a plurality of optical fibers, a waveguide, a plurality of waveguides, a mirror or a prism, for example.

In many embodiments, the multiplexed optical signal comprises a plurality of channels, in which each channel of the plurality corresponds to at least one frequency of the sound. The plurality of channels may correspond to at least about sixteen channels and said at least one frequency may correspond to at least about sixteen frequencies.

In many embodiments, the multiplexed optical signal is transmitted through the eardrum with a plurality of light sources, in which each light source is configured to transmit a light signal corresponding to said channel of the plurality such that said light source corresponds to said at least one frequency of sound. The plurality of light sources may comprise at least three light sources, and each of the at least three light sources can be configured to emit one or more wavelengths of light separate from the wavelengths of the other light sources.

In many embodiments, the multiplexed optical signal is transmitted through the eardrum of the user to at least one optical waveguide, the at least one optical waveguide affixed to the middle ear and coupled to an optical array positioned at least partially within the cochlea. The at least one waveguide may comprise at least one optical fiber and the optical array may comprise an array of openings configured to emit light from the at least one optical fiber. The at least one waveguide and optical array can be sized to pass through an incision in the eardrum.

In many embodiments, the multiplexed optical signal comprises a wavelength multiplexed optical signal, and the wavelength multiplexed optical signal comprises a plurality of wavelengths such that each wavelength corresponds to an opening of the array. Each wavelength of the plurality may correspond to an opening of the array. The at least one waveguide may comprise a plurality of waveguides, in which each waveguide of the plurality is coupled to a corresponding opening of the array and a corresponding wavelength of the plurality of wavelengths such that tissue stimulating light is passed through the opening in response to the wavelength. An optical structure can be positioned in the middle ear of the user to separate the wavelengths to correspond with each waveguide, and such that each separated wavelength corresponding to each waveguide is transmitted to said each waveguide based on the wavelength. A plurality of optical filters can be positioned in the middle ear of the user, and the wavelengths can be separated with the optical filters, in which each optical filter is positioned over one waveguide and configured to pass the wavelengths corresponding to the opening coupled to said one waveguide.

In many embodiments, a grating is configured to select the wavelengths of each waveguide to correspond to each opening.

In many embodiments, the multiplexed optical signal comprise a time division multiplexed signal. The time division multiplexed signal may comprise a plurality of time-slots, in which each time slot of the plurality corresponds to an opening of the array. The time division multiplexed signal may comprise a plurality of time slots and a clock signal, and circuitry can be coupled to the at least one waveguide and the optical array so as to receive the clock signal and divide the time division multiplexed signal among the openings of the array such that each time slot corresponds to an opening of the array. Each time slot may correspond to at least one frequency of the sound such that light is passed through each opening in response to a portion of the multiplexed signal corresponding to the time slot. The time division multiplexed signal can be pulse width modulated such that each timeslot of the plurality comprises a pulse of light having a duration that corresponds to light through the opening corresponding to said timeslot.

In many embodiments, a light source is positioned in the middle ear and coupled to the optical array positioned at least partially within the cochlea and wherein the light sources emits light in response to the time division multiplexed optical signal.

In many embodiments, a modulator is coupled to the light source, and the modulator adjusts the light beam to emit light from an opening of the at least one optical fiber in response to the time division multiplexed optical signal. The at least one optical waveguide may comprise a plurality of wavelength selective optical waveguides, and the modulator can adjust a wavelength of the light to direct the light substantially along each of the wavelength selective optical waveguides to an opening on a distal end of said waveguide. The light source may comprise a laser and the opening may comprise a plurality of openings disposed along the at least one waveguide. The modulator can be configured to adjust a mode structure of the laser to transmit light selectively through each of the plurality of openings. The mode structure may comprise a first mode structure and a second mode structure, and the plurality of openings may comprise a first opening and a second opening, and the at least one waveguide can be configured to emit light substantially through the first opening in response to the first mode structure and through the second opening in response to the second mode structure.

In many embodiments, the multiplexed optical signal is transmitted to at least one optical fiber extending into the cochlea. The at least one optical fiber can be sized to pass through an incision in the middle ear. The at least one optical fiber may comprise a plurality of optical fibers extending into the cochlea, in which each fiber corresponds to at least one frequency of the sound. Each fiber can be configured to stimulate the cochlea at a predetermined location of the cochlea corresponding to a corresponding range of frequencies in response to the at least one frequency of the sound.

In many embodiments, the multiplexed optical signal is transmitted through at least one of an opening or a window in the eardrum.

In many embodiments, the optical array, the at least one waveguide, and the demultiplexer comprise substantially non-magnetic materials configured for MRI imaging when implanted in the user.

In another aspect embodiments of the present invention provide system to stimulate tissue. A plurality of openings are configured for placement at least partially within the tissue. Circuitry is configured to receive a signal from a source. At least one light source is coupled to the circuitry and configured to emit a multiplexed optical signal comprising a plurality of light pulses. At least one waveguide is configured to receive the multiplexed optical and pass light through the openings in response to the light pulses to stimulate the tissue.

In another aspect embodiments of the present invention provide, a system to transmit an audio signal to a user. An optical array comprises a plurality of openings configured for placement at least partially within a cochlea of the user. Circuitry is configured to receive the audio signal from a sound source. At least one light source coupled to the circuitry and configured to emit a multiplexed optical signal comprising a plurality of light pulses. At least one waveguide is configured to receive the multiplexed optical signal and pass light through the openings in response to the light pulses.

In many embodiments, the circuitry is configured to determine widths of a plurality of light pulses, and each light pulse corresponds to an opening of the array. A width of said each light pulse corresponds to an amount of light through said corresponding opening of the array.

In many embodiments, the circuitry is configured to determine frequencies of the audio signal and wherein the frequencies correspond to openings of the array and wherein the circuitry is configured to determine a width of each pulse in response to one or more of the frequencies.

In many embodiments, the at least one light source comprises a plurality of light sources and wherein each light source corresponds to one opening of the array. Each of the plurality of light sources can be configured to emit light comprising wavelengths substantially separated from wavelengths of other light sources of the plurality. The plurality of light sources may comprise at least three light sources and the optical array may comprise at least three openings, and each of the at least three light sources may correspond to one opening of the at least three openings of the array.

In many embodiments, each of the at least three light sources is configured to emit light comprising wavelengths substantially separated from others of the at least three light sources, and the wavelengths of each source correspond to one opening of the at least three openings.

In many embodiments, the at least one waveguide comprises a plurality of waveguides and wherein each waveguide of the plurality corresponds to one opening of the array. The plurality of light waveguides may comprise at least three light waveguides and the optical array comprises at least three openings and wherein each of the at least three light waveguides corresponds to one opening of the at least three openings of the array.

In many embodiments, an optical structure is configured to receive the multiplexed optical signal. The optical structure is configured for placement in the middle and configured to select wavelengths of the multiplexed signal. The optical structure is sized to pass through an incision in the eardrum for placement in the middle ear and wherein the optical array is sized for placement at least partially inside the cochlea through a round window of the cochlea. The optical structure may comprise at least one of an optical filter, a grating, an etalon, a plurality of optical fibers, or a prism. The multiplexed optical signal may comprise a plurality of optical channels, in which each optical channel of the plurality corresponding to at least one frequency of the sound. The plurality of optical channels may correspond to at least about sixteen channels and said at least one frequency corresponds to at least about sixteen frequencies.

In many embodiments, an elongate optical transmission structure is configured for placement at least partially within the ear canal of the user and the elongate optical transmission structure is configured to transmit multiplexed optical signal through the eardrum.

In many embodiments, the multiplexed optical signal is transmitted through the eardrum of the user to at least one waveguide, and the at least one waveguide is affixed to the middle ear and coupled to an optical array positioned at least partially within the cochlea. The at least one waveguide and the optical array can be sized to pass through an incision in the eardrum. The multiplexed optical signal may comprise a wavelength multiplexed optical signal, and the wavelength multiplexed optical signal may comprise a plurality of wavelengths such that each wavelength corresponds to an opening of the array. Each wavelength of the plurality may correspond to an opening of the array. The plurality of wavelengths may comprise at least three wavelengths, and the plurality of openings may comprise at least three openings. Each wavelength of the plurality may correspond to one opening of the at least three openings.

In many embodiments, the circuitry is configured to transmit a series of the light pulses to correspond to openings of the array. The series may comprise a plurality of pulses, and each pulse of the plurality may correspond to one opening of the plurality of openings. The plurality of openings may comprise at least three openings, and the series may comprises at least three pulses, such that each pulse of the at least three pulses corresponds to one opening of the at least three openings.

In many embodiments, the series comprises a timing pulse. The timing pulse may comprise a substantially fixed width, and the timing pulse may comprise energy to power circuitry coupled to the plurality of openings.

In many embodiments, switching circuitry is coupled to the at least one waveguide to couple sequentially each opening of the plurality to the at least one waveguide in response to the timing pulse such that each pulse of the series corresponds to one opening of the plurality. The series of pulses may comprise a pre-determined order and timing of the pulses, and the switching circuitry may comprise a timer coupled to switches to open the switches and close the to correspond with pulses of the series. The series may comprise at least three pulses, and the switching circuitry can be configured to coupled at least one waveguide sequentially to each opening of the at least three such that each pulse of the series corresponds to one opening of the plurality.

In many embodiments, a light source is positioned in the middle ear and coupled to the optical array positioned at least partially within the cochlea, and the light source emits light in response to the time division multiplexed optical signal.

In many embodiments, a modulator is coupled to the light source, and the modulator adjusts the light beam to emit light from an opening of the at least one optical fiber in response to the time division multiplexed optical signal. The at least one optical waveguide may comprise a plurality of wavelength selective optical waveguides, and the modulator can adjust a wavelength of the light to direct the light substantially along one of the wavelength selective optical waveguides to an opening on a distal end of the waveguide.

In many embodiments, the light source comprises a laser and the opening comprises a plurality of openings disposed along the at least one waveguide, and the modulator is configured to adjust a mode structure of the laser to transmit light substantially through one of the plurality of openings.

In many embodiments, the optical array, the at least one waveguide, and the demultiplexer comprise substantially non-magnetic materials configured for MRI imaging when implanted in the user.

In another aspect embodiments provide a method of providing a hearing prosthesis for a user. An incision is made in an eardrum of the user, in which the eardrum comprises an annulus. An optical array, at least one waveguide, and a demultiplexer are passed through the incision.

In many embodiments, the incision extends at least partially through the annulus.

In many embodiments, the eardrum is positioned to a side of an ear canal to pass the optical array, the demultiplexer and the at least one waveguide through the incision. The at least one waveguide and the demultiplexer can be affixed to the middle ear of the user.

In many embodiments, the optical array is positioned at least partially through a round window, and the at least one waveguide and the demultiplexer are positioned in a middle ear of the user. The at least one waveguide and the demultiplexer may be affixed to the middle ear of the user.

In many embodiments, the at least one waveguide comprises at least three waveguides. The demultiplexer may comprise an optical demultiplexer. The optical demultiplexer may comprise at least three filters to separate at least three wavelengths of light.

In many embodiments, the demultiplexer comprises switching circuitry and a timer. The optical array, the at least one photodetector, and the demultiplexer can be passed through the incision comprise substantially non-magnetic materials configured for MRI imaging.

In another aspect, embodiments provide a device to stimulate tissue. The device comprises means for generating a multiplexed optical signal; and means for stimulating tissue in response to the optical signal. The means for generating the multiplexed optical signal may comprise one or more of the structures as described herein so as to generate the multiplexed optical signal, for example the multiplexers. The means for stimulating tissue in response to the multiplexed optical signal may comprise one or more of the structures as described herein for stimulating tissue in response to the optical signal, for example the waveguide.

BRIEF DESCRIPTION OF THE DRAWINGS

FIG. 1A1 shows an optically coupled cochlear implant system comprising an ear canal module, in accordance with embodiments of the present invention;

FIG. 2A shows an input transducer assembly configured to emit a wavelength multiplexed optical signal in accordance with embodiments of the present invention;

FIG. 2A1 optical pulses comprising separate wavelengths of light of a wavelength multiplexed optical signal as in FIG. 2A;

FIG. 2A2 shows an optical multiplexer configured to wavelength multiplex light from a plurality of light sources having separate wavelengths, as in FIG. 2A;

FIG. 3A1 optical pulses comprising a series of pulses of the time multiplexed optical signal as in FIG. 3A;

FIG. 3A2 shows a clock pulse of the series of optical pulses of the time multiplexed optical signal as in FIG. 3A.

DETAILED DESCRIPTION OF THE INVENTION

The present invention relates to tissue stimulation with light generally, and more specifically to stimulation of the cochlea for hearing. Although specific reference is made to cochlear implants, embodiments of the present invention can be used in many applications wherein tissue is stimulated, for example with stimulation of muscles, nerves and neural tissue, for example the treatment of Parkinson's.

As used herein light encompasses infrared light, visible light and ultraviolet light.

Figure 1A:
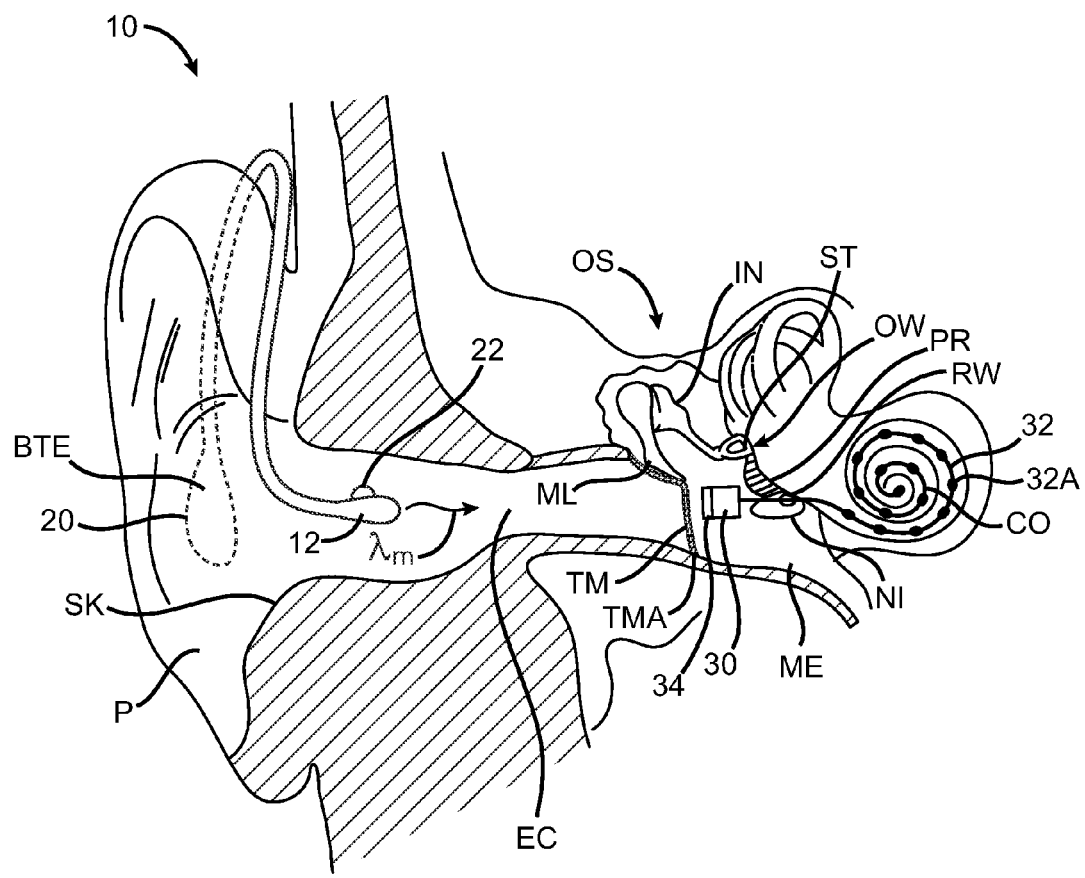
FIG. 1A shows an optically coupled cochlear implant system comprising a behind the ear unit, in accordance with embodiments of the present invention.

FIG. 1A shows an optically coupled cochlear implant system 10 comprising an input transducer assembly 20 and an output assembly 30. The input transducer assembly 20 may comprise behind the ear unit (hereinafter "BTE"). The BTE unit can be positioned behind a pinna P of the user, so as to decrease visibility of the BTE unit. The BTE unit can house electronics used to process and input signal. An input transducer, for example microphone 22, is coupled to the BTE unit and can transmit an audio signal to the BTE unit. The BTE can convert the input signal into a multiplexed optical signal $\lambda_M$. The BTE unit can be coupled to an optical transmission structure 12 to emit the multiplexed optical signal $\lambda_M$. The light transmission structure 12 can extends from the BTE into the ear canal EC. The light transmission structure 12 may support microphone 22. Microphone 22 can be positioned in many locations, for example within the ear canal or near the ear canal opening to detect sound localization cues. Alternatively, the microphone may be positioned on the ear canal. The input transducer may comprise a second microphone positioned on the BTE unit for noise cancellation. The sound input may comprise sound from a Bluetooth connection, and the BTE may comprise circuitry to couple with a cell phone, for example.

The output assembly 30 is configured for placement in the middle ear cavity and cochlea of the user. The output assembly 30 comprises at least one waveguide 34 configured to receive the multiplexed optical signal $\lambda_M$. The output assembly comprises an optical array 32 coupled to the at least one waveguide 34 so as to stimulate the cochlea in response to the multiplexed optical signal $\lambda_M$. The optical array comprises a plurality of openings 32A, for example 16 openings. The openings may comprise openings to an optical fiber, such that the optical fiber can emit light at the opening, for example an opening formed in a cladding of the fiber. Alternatively or in combination, the opening may comprise an end of the optical fiber configured to emit light into tissue of the cochlea near the fiber. The output assembly 30 may comprise a demultiplexer coupled to the at least one waveguide to demultiplex the optical signal. The multiplexed optical signal may comprise, for example, a time multiplexed optical signal or a wavelength multiplexed optical signal. The demultiplexer comprises structures so as to demultiplex the optical signal and stimulate tissue of the cochlea. The demultiplexer can be configured to coupled pulses of the multiplexed optical signal with apertures of the array such that pulses of the multiplexed optical signal correspond to apertures of the array.

The output assembly 30 may comprise many known biocompatible and substantially non-magnetic materials, such that output assembly 30 is configured for use with MRI imaging when implanted in the patient. For example the optical array 32 may comprise substantially non-magnetic conducting material, such as at least one of glass, fluorozirconate, fluoroaluminate, chalcogenide glass or plastic. The optical array may comprise a biocompatible substantially non-magnetic housing material, for example at least one of silicone elastomer, biocompatible plastic, or hydrogel.

The optical array 32 and at least one waveguide 34 can be configured in many ways to stimulate the cochlea. For example, the apertures can be coupled to the waveguide.

FIG. 1A1 shows an optically coupled cochlear implant system comprising an ear canal module (hereinafter "ECM"). The ECM may comprise many of the components of the BTE unit and vice-versa. The ECM may be shaped from a mold of the user's ear canal EC. Circuitry (CR) can be coupled to microphone 22. The circuitry may comprise a sound processor. The ECM may comprise an energy storage device PS configured to store electrical energy. The storage device may comprise many known storage devices such at least one of a battery, a rechargeable batter, a capacitor, a supercapacitor, or electrochemical double layer capacitor (EDLC). The ECM can be removed, for example for recharging or when the user sleeps. The ECM may comprise a channel 29 to pass air so as to decrease occlusion. Although air is passed through channel 29, feedback is substantially non-existent due to the electrical and non-acoustic stimulation of the cochlea.

The energy storage device PS may comprise a rechargeable energy storage device that can be recharged in many ways. For example, the energy storage device may be charged with a plug in connector coupled to a super capacitor for rapid charging. Alternatively, the energy storage device may be charged with an inductive coil or with a photodetector PV.

The photodetector detector PV may be positioned on a proximal end of the ECM such that the photodetector is exposed to light entering the ear canal EC. The photodetector PV can be coupled to the energy storage device PS so as to charge the energy storage device PS. The photodetector may comprise many detectors, for example black silicone as described above. The rechargeable energy storage device can be provided merely for convenience, as the energy storage device PS may comprise batteries that the user can replace when the ECM is removed from ear canal.

The photodetector PV may comprise at least one photovoltaic material such as crystalline silicon, amorphous silicon, micromorphous silicon, black silicon, cadmium telluride, copper indium gallium selenide, and the like. In some embodiments, the photodetector PV may comprise black silicon, for example as described in U.S. Pat. Nos. 7,354,792 and 7,390,689 and available under from SiOnyx, Inc. of Beverly, Mass. The black silicon may comprise shallow junction photonics manufactured with semiconductor process that exploits atomic level alterations that occur in materials irradiated by high intensity lasers, such as a femto-second laser that exposes the target semiconductor to high intensity pulses as short as one billionth of a millionth of a second. Crystalline materials subject to these intense localized energy events may under go a transformative change, such that the atomic structure becomes instantaneously disordered and new compounds are "locked in" as the substrate re-crystallizes. When applied to silicon, the result can be a highly doped, optically opaque, shallow junction interface that is many times more sensitive to light than conventional semiconductor materials. Photovoltaic transducers for hearing devices are also described in detail in U.S. Patent Applications No. 61/073, 271, entitled "Optical Electro-Mechanical Hearing Devices With Combined Power and Signal Architectures"; and 61/073,281, entitled "Optical Electro-Mechanical Hearing Devices with Separate Power and Signal", the full disclosures of which have been previously incorporated herein by reference and may be suitable for combination in accordance with some embodiments as described herein.

The BTE may comprise many of the components of the ECM, for example photodetector PV, energy storage device PS, the processor and circuitry, as described above.

Figure 1B:
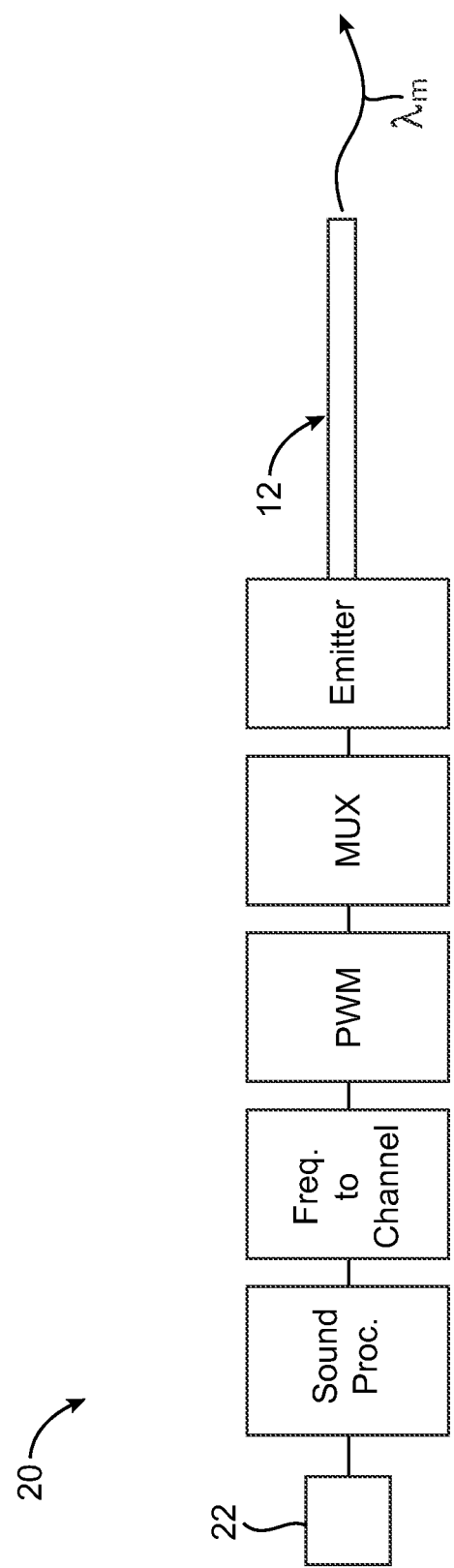
FIG. 1B shows an input transducer assembly configured to emit a multiplexed optical signal, in accordance with embodiments of the present invention.

FIG. 1B shows input transducer assembly 20 configured to emit a multiplexed optical signal. The components of the input transducer assembly may be housed in BTE unit or in the ECM, or a combination thereof. Microphone 22 is coupled to a sound processor. The sound processor may comprise one or more of many commercially available sound processors. The sound processor comprises a tangible medium to store instructions of a computer program embodied therein. The sound processor may comprise or be coupled to a multi-band frequency to channel converter. The frequency to channel converter can convert frequencies of the audio signal to filtered sound channels corresponding to locations of the cochlea for electrical stimulation such that the user perceives the sound of the audio signal. The circuitry of the input assembly may comprise pulse width modulation (hereinafter "PWM") circuitry. The PWM circuitry can be configured to determine the width of each optical pulse corresponding to one of the apertures of the array. The width of the optical pulse can be determined in response to the frequency of the sound corresponding to the electrode that is coupled to the optical pulse. A multiplexer MUX and an emitter are coupled to the PWM circuitry.

The emitter comprises at least one light source. The at least one light source emits pulses of light having a duration determined by the PWM circuitry. The width of the pulse refers to the duration of the pulse. With serial multiplexing, the at least one light source may comprise a single light source, and the timing of the pulses is determined by the multiplexer. With optical multiplexing, the at least one light source comprises a plurality of light sources, for example at least three light sources. The plurality of light sources can be configured to emit light pulses substantially simultaneously, or sequentially to decrease peak power consumption of the plurality of light sources.

The emitter is coupled to an optical transmission structure 12. The optical transmission structure may comprise an optical fiber, a plurality of optical fibers, a window, or an opening in the ECM. The multiplexed light is transmitted from the optical transmission structure 12 toward tissue, for example tissue of the eardrum TM, although light can be transmitted through other tissue, for example bone of openings formed in bone to transmit light.

FIG. 2A shows an input transducer assembly 20 configured to emit a wavelength multiplexed optical signal. The sound processor can determine the frequencies of the audio signal. The multi-band filtered audio signal can be converted to channels of the optical array and corresponding wavelengths with a frequency to wavelength converter (Freq. to λ). The width of each pulse for each wavelength is determined for a plurality of wavelengths, for example at least three wavelengths. Although sixteen wavelengths are shown, many more channels can be stimulated, for example up 32. The plurality of light sources comprises a first light source configured to emit first wavelengths $\lambda 1$, a second light source configured to emit second wavelengths $\lambda 2$, a third light source configured to emit third wavelengths $\lambda 3$ and . . . a sixteenth light source configured to emit sixteenth wavelengths $\lambda 16$. Light from each source is emitted to an optical multiplexer. The optical multiplexer may comprise many known methods of optical multiplexing. For example the optical multiplexer may comprise at least one of a grating, an etalon, a prism, an optical fiber, a waveguide, a nanostructure, or a plurality of optical fibers.

FIG. 2A1 optical pulses comprising separate wavelengths of light of a wavelength multiplexed optical signal as in FIG. 2A. A first pulse P1 comprises first wavelengths of light and a first width W1. A Second pulse P2 comprises second wavelengths of light and a second width. A third pulse P3 comprises third wavelengths of light and a third width. A fourth pulse P4 comprises fourth wavelengths of light and a fourth width. Additional pulses, for example a total of 16 or more, can be transmitted.

Each of the pulses comprise substantially separate pulses of light such that the pulses can be separated with the demultiplexer so as to correspond with one electrode of the array, or a pair of apertures of the array. The wavelengths of each source may comprise wavelengths of a laser, in which the wavelengths of the laser correspond to the band width of the laser beam.

FIG. 2A2 shows an optical multiplexer configured to multiplex light from a plurality of light sources having separate wavelengths as in FIGS. 2A and 2A1. Light from the sources can be emitted toward an optical structure grating, for example, and combined with optical transmission structure 12. The multiplexed signal can travel along optical transmission structure 12 toward the output assembly 30. The light for each channel of the multiplexed optical signal can be emitted serially from each source, so as to decrease peak power consumption of the light sources. For example the first light source can emit a first light pulse of the packet, followed by the second light source emitting the second light source of the packet until each of the light sources corresponding to one of the channels has emitted the corresponding pulse width modulated light signal of the packet. In many embodiments, each light source emits laser light when the other light sources of the optical multiplexer do not emit light. Thus serial use of the light sources can ensure that the power storage device can provide sufficient electrical energy to each of the light sources.

Figure 2B:
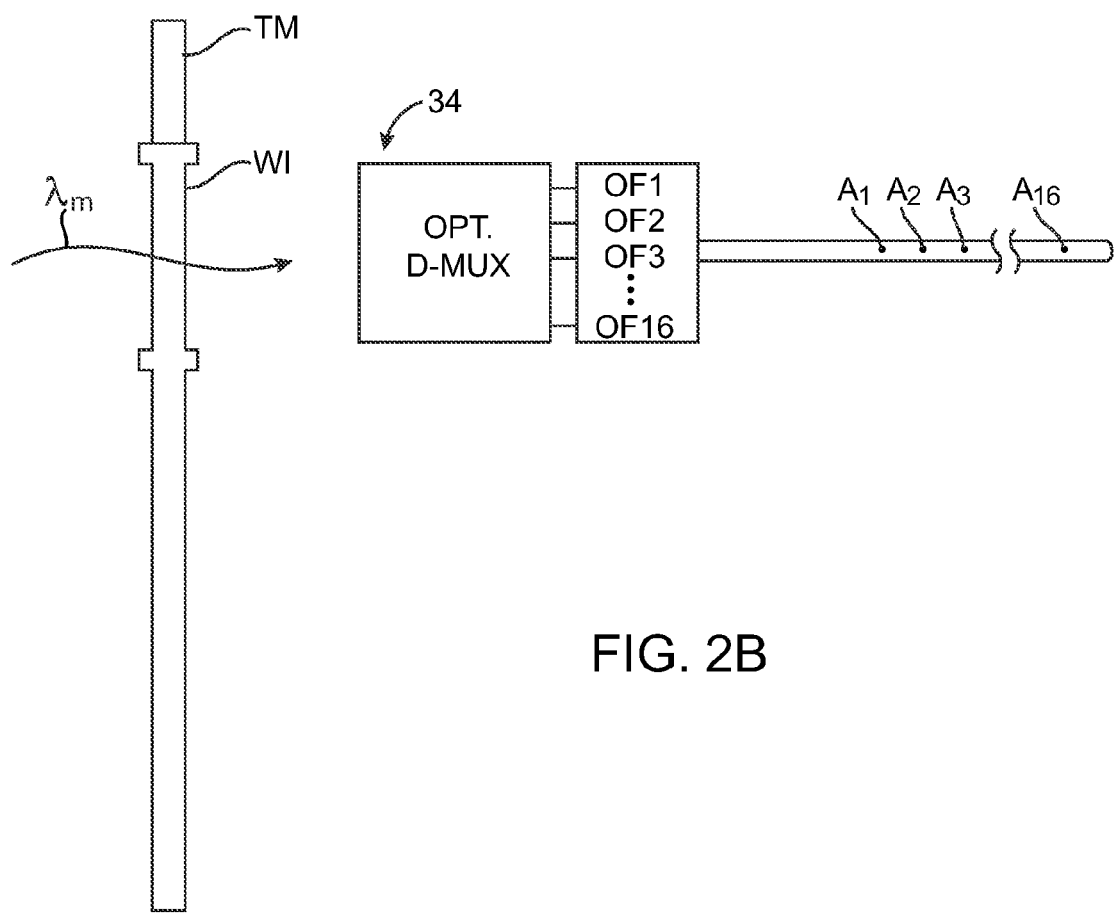
FIG. 2B shows an output assembly comprising an optical demultiplexer configured to couple with an input transducer assembly as in FIG. 2A.

FIG. 2B shows an output assembly configured to couple with an input transducer assembly as in FIG. 2A. The output assembly comprises at least one waveguide 34 configured to receive the multiplexed optical signal. The at least one waveguide may comprise a plurality of waveguides, such as a first waveguide, for example first optical fiber OF1, a second waveguide, for example second optical fiber OF2, a third waveguide, for example third optical fiber OF3 . . . and a sixteenth waveguide, for example sixteenth optical fiber OF16. Additional or fewer waveguides may be used and may comprise many known materials. An optical multiplexer can be positioned to receive the multiplexed signal beam and separate the multiplexed optical signal. The optical demultiplexer may comprise many known optical elements such as prisms, gratings, mirrors, optical fibers, waveguides, nanostructures, filters, band-pass filters, etc. as described above.

Each of the waveguides extends from the demultiplexer to a corresponding opening. Each of the optical fibers may have a first end coupled to the demultiplexer and a second end coupled to the opening at the distal end of the optical array, so as to stimulate tissue. First optical fiber OF1 extends to a first opening A1. Second optical fiber OF2 extends to a second opening A2. Third optical fiber OF3 extends to a third opening A3. Sixteenth optical fiber OF16 extends to a sixteenth opening A16.

The multiplexed optical signal can be transmitted through tissue. For example, the multiplexed optical signal can be transmitted through an eardrum TM of the user. Alternatively or in combination, the multiplexed optical signal can be transmitted through a window WI formed in the eardrum, or an opening formed in the eardrum. The window can be helpful to maintain coherence and wavefront properties of the multiplexed optical signal. However, many embodiments do not include such structures in the eardrum.

Figure 2C:
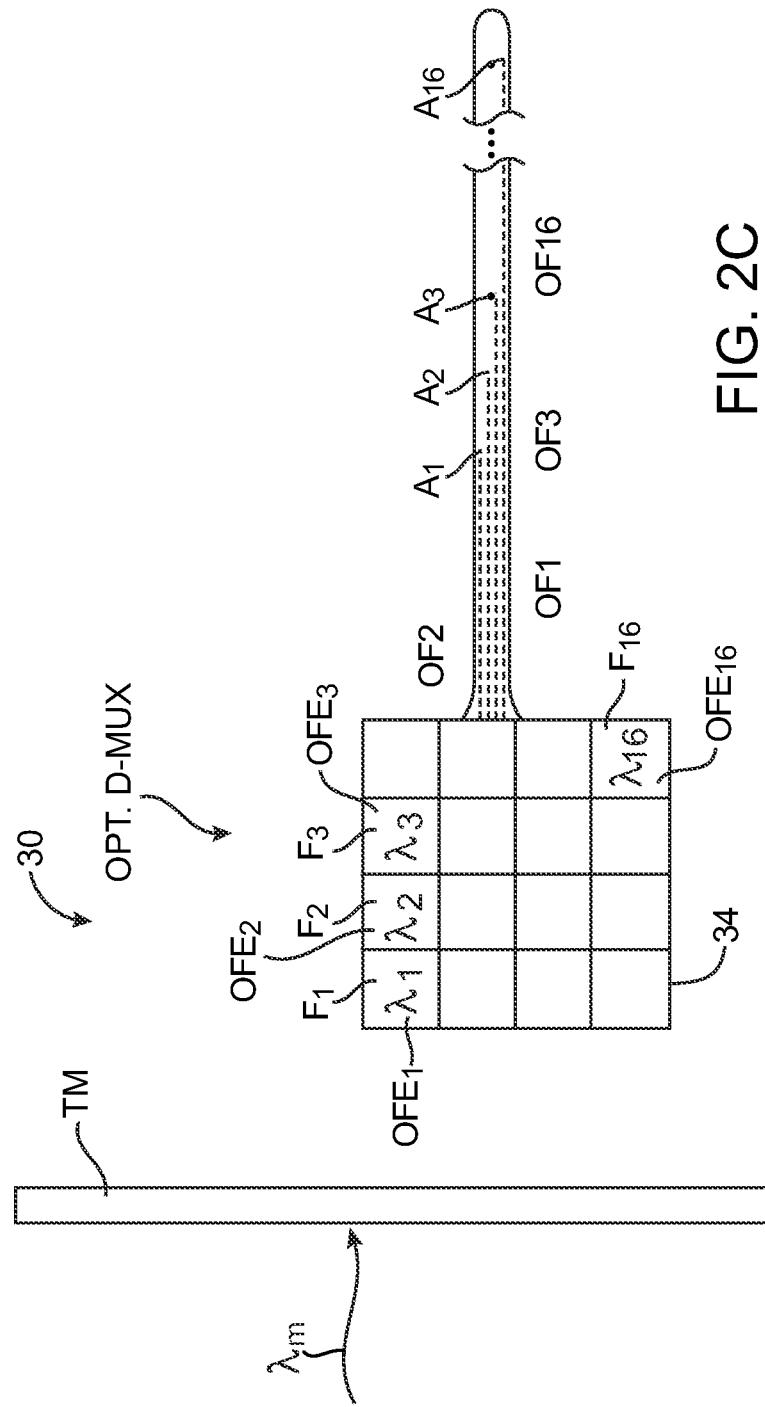
FIG. 2C shows an output assembly comprising an optical demultiplexer comprising optical filters and an array of waveguides, in accordance with embodiments.

FIG. 2C shows an output assembly 30 comprising an optical demultiplexer comprising optical filters and an array of waveguides. The at least one waveguide 34 may comprise the array of waveguides. The array of waveguides comprises a optical fiber end OFE1, a second optical fiber end OF2, a third optical fiber end OF3 . . . and a optical fiber end OF16. Additional or fewer optical fibers can be included in the array, for example 32 waveguides. The optical multiplexer may comprise optical filters positioned in front of the proximal end of each optical fiber to filter light transmitted to each optical fiber. The optical multiplexer may comprise a first optical filter F1, a second optical filter F2, a third optical filter F3 . . . and a sixteenth optical filter F16. This configuration can separate the light into channels transmitted to each optical fiber. For example, each filter can transmit wavelengths of light that are substantially separate from the wavelengths of light transmitted by the other filters. The optical array of optical fibers comprises a first opening A1 on a distal end of first optical fiber OF1, a second opening A2 on a distal end of second optical fiber OF2, a third opening A3 on a distal end of third optical fiber OF3 . . . and a sixteenth opening A16 on a distal end of sixteenth of optical fiber OF16.

Each of the proximal ends is coupled to a corresponding opening of the optical array. First optical fiber end OFE1 is coupled to first opening A1 so as to comprise a first channel. Second optical fiber end OFE2 is coupled to second opening A2 so as to comprise a second channel. Third optical fiber end OFE3 is coupled to third opening A3 so as to comprise a third channel. The output assembly may comprise additional channels. For example, sixteenth optical fiber end OFE16 is coupled to sixteenth opening A16 so as to comprise a sixteenth channel. Additional or fewer channels can be provided.

The perception of loudness due to electrical stimulation of the cochlea with openings 32A can depend on many factors including cochlear location, pulse width (duration) and pulse height (intensity). For pulses that are 50 us, for example, for a very loud sound. For a soft sound, only a 10 us pulse can be sufficient. Increasing the width of the pulse can decrease the required amplitude of light. A person of ordinary skill in the art can conduct experimental studies to determine empirically based on the teachings described herein, the intensity of the light energy to produce the sensation of sound.

Waveguides can be configured to generate light at the tissue stimulating region of the cochlea, such that the user perceives sound in response to the light energy. Based on the teaching described herein, a person of ordinary skill in the art can determine empirically the size of the waveguides, the intensity and duration of the light pulses to provide a full spectrum of sound from soft to loud.

The light source and optical multiplexer of the input assembly can be configured in many ways to provide bandwidths suitable for use with two overlapping detector arrays. The light source and multiplexer can be combined with known wavelength multiplexing systems suited for incorporation in accordance with embodiments as described herein, such as components the EPIC integrated channelizer of the MIT Microphotonics Center and the photonics components available from Intel. The light source may comprise an integrated optical RF channelizer on silicon comprising an integrated photonics chip and laser light source, A first light laser source can be configured to emit light having wavelengths suitable for absorption with the first array, and the first light source can be coupled with a first modulator to modulate the first light beam so as to correspond to channels of the first array detector. A second light laser source can be configured to emit light having wavelengths suitable for transmission through the first array and absorption with the second array, and the second light source can be coupled with a second modulator to modulate the light beam so as to correspond to channels of the first array detector. The modulated light signals can be received by a multimode interferometeric splitter to demultiplex the transmitted light signal, for example. Transmission through an optical window or opening of the eardrum can retain integrity of the transmitted light.

Figure 3A:
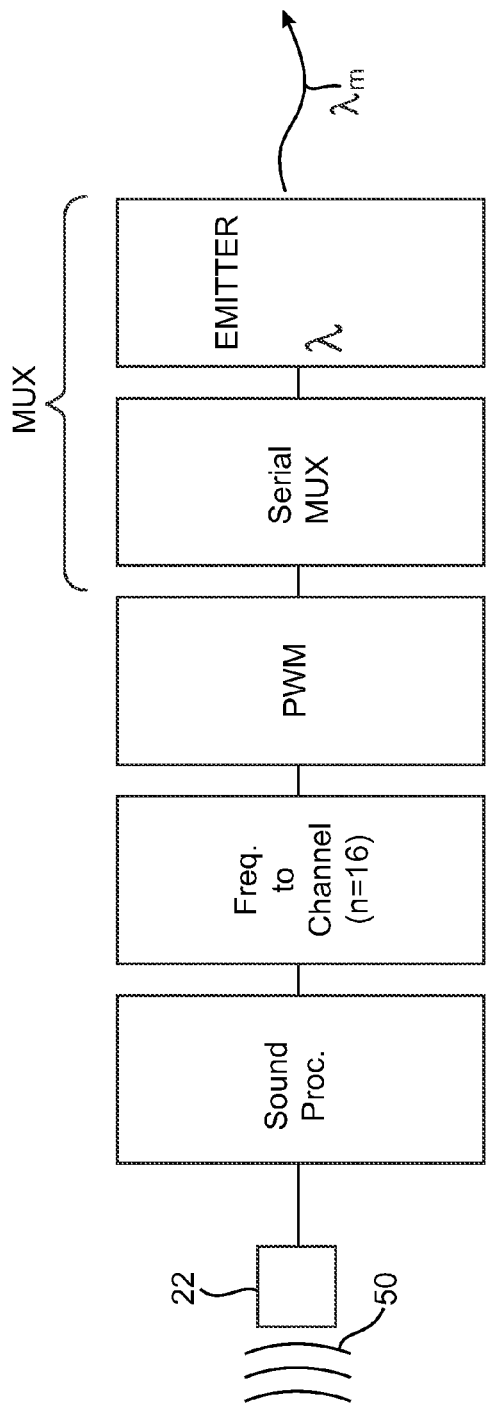
FIG. 3A shows an input transducer assembly configured to emit a time multiplexed optical signal in accordance with embodiments of the present invention.
Figure 3A:
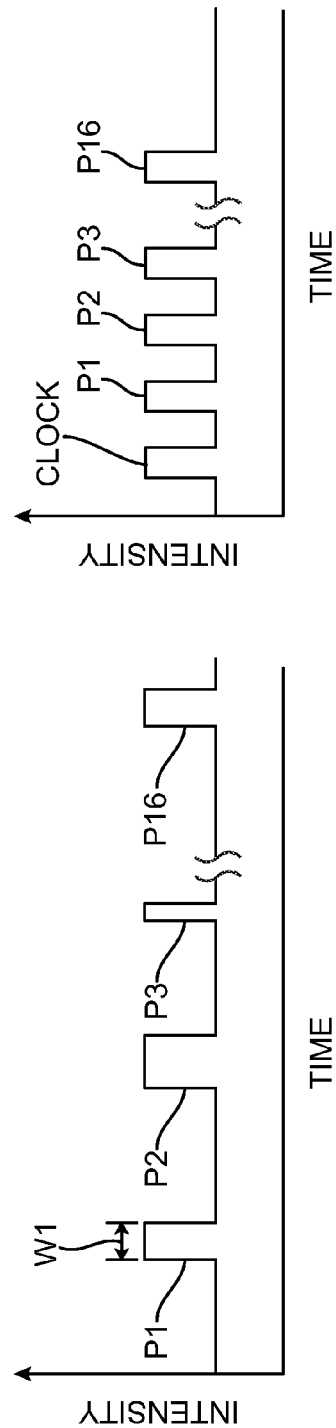

FIG. 3A shows an input transducer assembly configured to emit a time multiplexed optical signal. The multiplexed optical signal λM may comprise the time multiplexed optical signal, for example a serial multiplexed optical signal. An audio signal 50, for example a sound, is received by microphone 22. The audio signal comprises an input to the sound processor. The frequencies of the audio signal can be determined, for example with circuitry as described above. The frequencies of the audio signal can be used to determine the amount of stimulation for each electrode of the array, in which each electrode corresponds to a channel. The width of each optical pulse can be determined with the PWM circuitry. The PWM circuitry is coupled to a serial multiplexer to multiplex the pulses for each electrode. The serial multiplexed pulses are emitted from an emitter comprising the at least one light source. The at least one light source may comprise a single light source, such as an infrared laser diode.

FIG. 3A1 optical pulses comprising a series of pulses of the time multiplexed optical signal as in FIG. 3A. The multiplexed serial pulses comprise a first pulse P1, a first pulse P1, a second pulse P2, a third pulse P3 . . . and a sixteenth pulse P16. Each pulse corresponds to one electrode of the array. An amount of electrical current is determined by a width of the pulse. First pulse P1 comprises a first width W1. Second pulse P2 comprises a second width. Third pulse P3 comprises a third width. Sixteenth pulse P16 comprises a sixteenth width. The multiplexer can be configured to emit packets of pulses, in which each packet comprises pulse information for each electrode of the array. For example, a packet may comprise sixteen pulses for the sixteen apertures of the array. The serial multiplexer can be configured to emit the pulses of each packet so as to correspond with a predetermined timing and sequence of the pulses.

FIG. 3A2 shows a clock pulse of the series of optical pulses of the time multiplexed optical signal as in FIG. 3A. The clock pulse can synchronize the packet with the demultiplexer, such that the pulses are demultiplexed so as to correspond with the appropriate electrode. For example, pulse P1 may correspond with electrode E1. The clock pulse provide power to the demultiplexer circuitry.

Figure 3B:
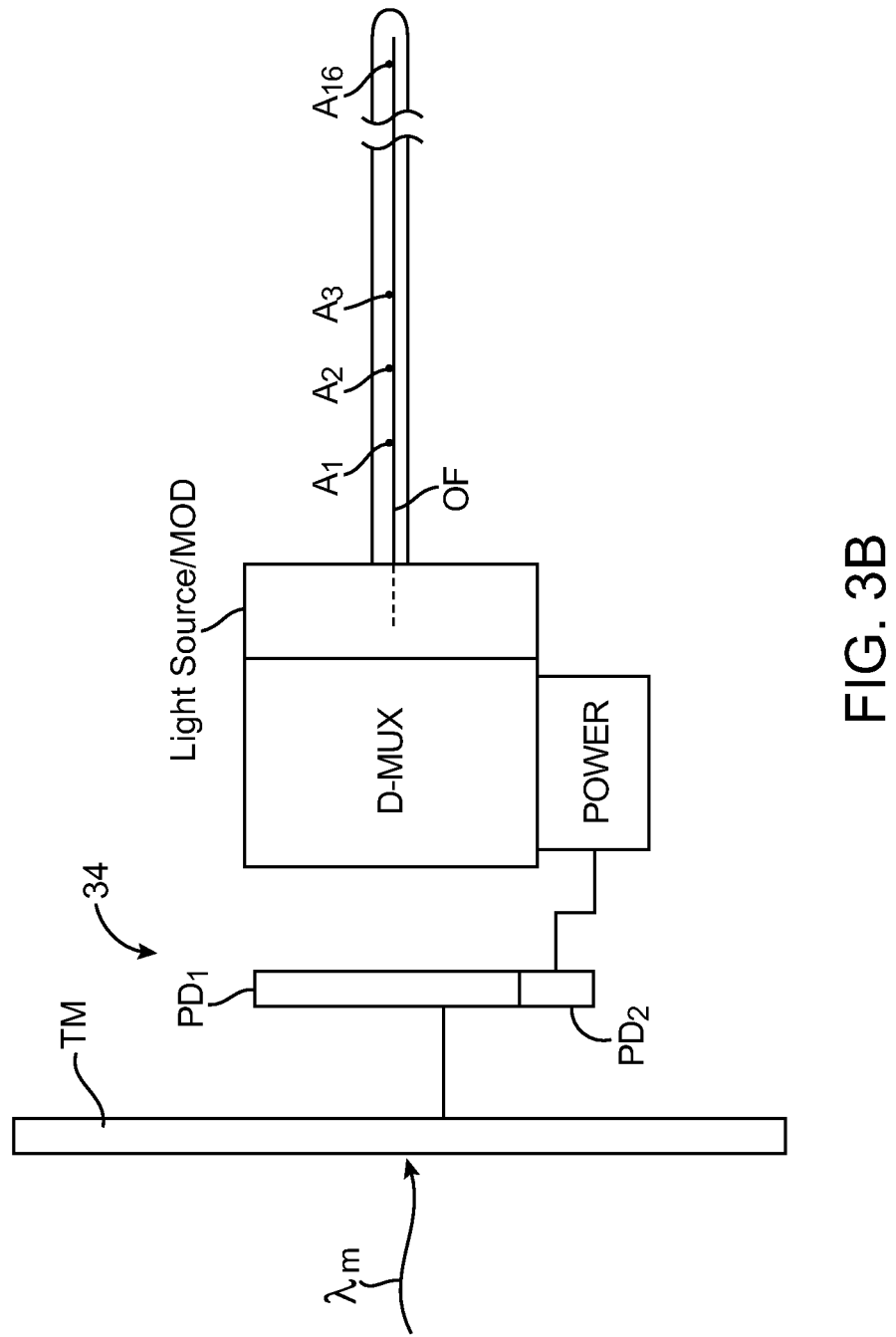
FIG. 3B shows an output assembly configured for use with an input transducer assembly as in FIG. 3A.

FIG. 3B shows an output assembly configured for use with an input transducer assembly as in FIG. 3A. The serial multiplexed optical signal is transmitted through the eardrum TM. The multiplexed optical signal is received by a photo detector PD1. Photodetector PD1 is coupled to demultiplexer circuitry D-MUX. The demultiplexer circuitry D-MUX can be coupled to a light source and optical modulator so as to emit a modulated beam along at least one optical fiber OF in response to the multiplexed light signal. The modulator can be configured to modulate the light beam of the source such that light is emitted substantially from one of the openings so as to stimulate neural tissue of the cochlea in proximity to the opening.

The circuitry D-MUX can be configured in many ways to demultiplex the optical signal. The circuitry D-MUX may comprise a timer and switches such that the multiplexer sequentially couples each electrode to the detector in accordance with a predetermined sequence such that the detector is coupled to one of the electrodes when the pulse corresponding to the electrode is incident on detector PD1. For example, the pulse sequence may comprise a packet of pulses as described above. The first pulse of the packet may comprise a clock pulse to power the circuitry and to reset the timer. The timer can be coupled to the switches of the multiplexer such that a switch corresponding to one electrode is closed when the optical pulse corresponding to the electrode arrives at the detector. The timer and switches may comprise low power circuitry, for example CMOS circuitry, such that the timer and switches can be power with the clock pulse. This can be helpful when the audio signal is weak such that the timer and switching circuitry has sufficient power. Power storage circuitry such as capacitors and super capacitors can be coupled to the detector PD1 to store energy from the clock pulse with power circuitry (Power). The power circuitry can be switched with the switching circuitry such that the power storage capacitors are decoupled from the detector PD1 when the light pulses for the electrodes arrive at detector PD1.

The output assembly can be configured in many ways to generate light in response to the multiplexed light signal. For example, the circuitry may comprise a light source and a modulator. The light source and modulator can be configured to emit light a series of light pulses corresponding to the openings of the optical fiber. The modulator can be configured to adjust the mode structure of the light source so as to emit light substantially from one of the apertures. The at least one optical fiber OF may comprise a plurality of waveguides, in which each waveguide is configured to transmit selectively light having a very narrow range of wavelengths. The modulator can adjust the wavelength of the light slightly such that light is transmitted along the waveguide corresponding to one of the openings so as to stimulate tissue with the narrow wavelengths of light corresponding to the channel of the opening.

A light source can be positioned in the middle ear and coupled to the optical array positioned at least partially within the cochlea. The light source in the middle ear can emit light in response to the time division multiplexed optical signal. A modulator can be positioned in the middle ear and coupled to the light source. The modulator can adjust the light beam to emit light from an opening of the at least one optical fiber in response to the time division multiplexed optical signal. The at least one optical waveguide may comprise a plurality of wavelength selective optical waveguides, for example photonic waveguides. The modulator can adjust a wavelength of the light to direct the light substantially along one of the wavelength selective optical waveguides to an opening on a distal end of the waveguide.

The light source may comprise a laser, and the opening may comprise a plurality of openings disposed along the at least one waveguide. The modulator can be configured to adjust a mode structure of the laser to transmit light substantially through one of the plurality of openings to stimulate the tissue, for example nerve tissue of the cochlea.

The serial light source and detector components may comprise silicon photonics components of the MIT Microphotonics Center and the photonics components commercially available from Intel, as described above.

In some embodiments, the power circuitry can be coupled to a separate detector PD2. The separate power and signal can be used to power the timing and switching circuitry.

The switching circuitry may comprise optical switches, for example an liquid crystal material, to switch the light signal transmitted to the optical fibers.

Figure 4A:
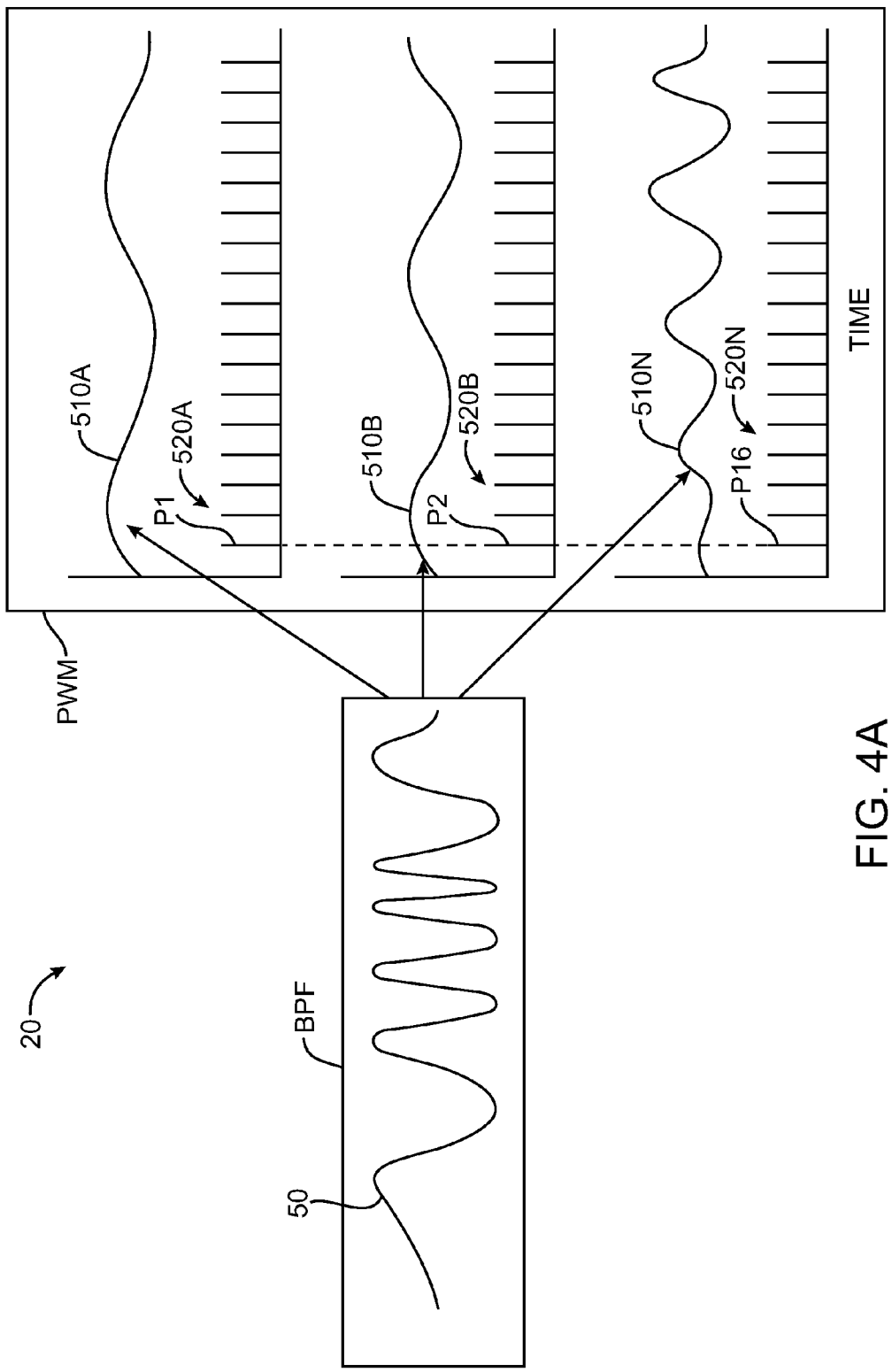
FIG. 4A shows signal to channel conversion with bandpass filtering and pulse width modulation so as to maintain substantially phase of the audio signal among the channels with high frequency stimulation of the cochlea, in accordance with embodiments.

FIG. 4A shows signal to channel conversion with bandpass filtering and pulse width modulation so as to maintain substantially phase of the audio signal among the channels with high frequency stimulation of the cochlea. The audio sound signal 50 may comprise a base band audio signal. Work in relation to embodiments as described herein indicates that the cochlea can respond to high frequency electrical stimulation so as to low pass filter the high frequency stimulation and demodulate the high frequency signal to the base band audio signal, such that the person can perceive sound based on the electrical stimulation, for example electrical stimulation having frequencies above the range of hearing of the patient. For example, with stimulation of high frequencies above about 10 kHz, for example above about 20 kHz, the cochlea can low pass filter and demodulate the high frequency signal into the base band audio sound signal such that the patient hears the sound with amplitude and phase of the base band audio signal. When these high frequencies comprise phase encoded information of the audio signal, the user can hear the audio signal with the corresponding amplitude and phase. The high frequency signal above about 10 kHz, for example above 20 kHz, such as 40 kHz or 100 kHz, or more, may comprise a pulse width modulated signal with amplitude and phase encoding with high frequencies, and the stimulation of the cochlea with the width modulated pulses at these high frequencies can result in demodulation of the high frequency pulse width modulated signal back into an audio band signal corresponding to the frequencies of the bandpass filtered channel. This demodulation of the high frequency amplitude and phase encoded signal can maintain both the amplitude and phase of the audio signal perceived by the user.

The audio signal 50 corresponding to a sound may comprise many frequencies and can be input into a bandpass filter BPF. The bandpass filter BPF may provide as output a first channel comprising a first band pass audio signal 510A comprising a first range of frequencies, a second channel comprising a second band pass audio signal 510B comprising a second range of frequencies, and an Nth channel comprising an Nth band pass audio signal 510A comprising an Nth range of frequencies. Each of the signals may comprise a substantially similar phase such that the phase of the BPF output is substantially maintained.

The audiosignal of each channel is converted to a pulse with modulated signal such that the phase of the original audio signal 50 is maintained among the channels. First bandpass audiosignal 510A corresponds to a first series 520A of width modulated pulses. Second bandpass audiosignal 510B corresponds to a second series 520B of width modulated pulses. Nth bandpass audiosignal 510N corresponds to an Nth series 520N of width modulated pulses. Each of the pulses may be determine so as to correspond to a substantially synchronous time base, such that each of the phase and amplitude of the original signal is maintained. For example, each of the pulses may be output to a corresponding light source to drive a corresponding photodetector, as described above. The Nth channel may comprise an eight channel, a sixteenth channel, a thirty second channel or a sixty fourth channel for example.

Figure 4B:
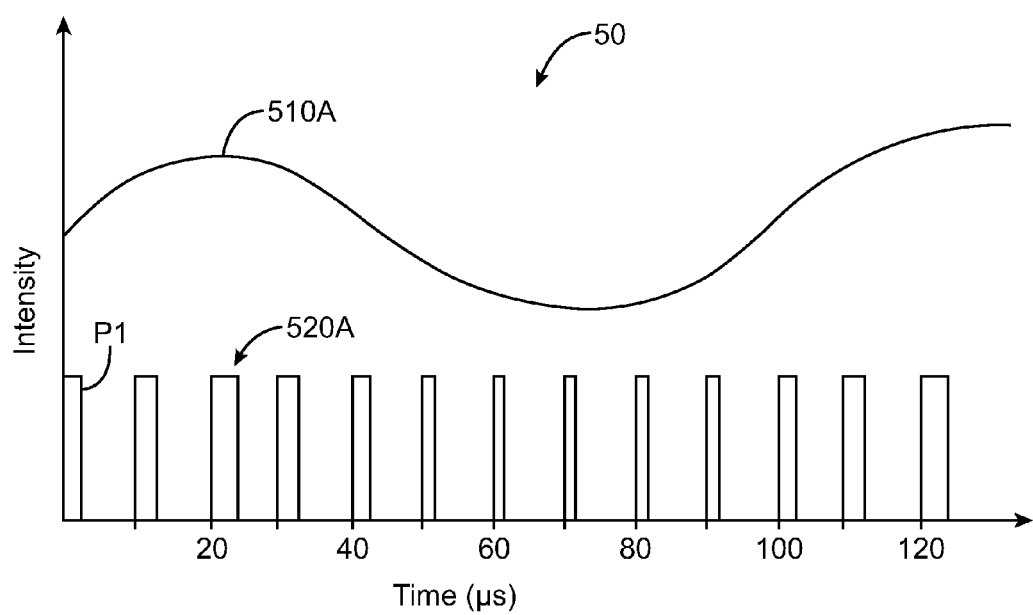
FIG. 4B shows pulses of a channel for high frequency stimulation of the cochlea so as to maintain phase of the audio signal as in FIG. 4A.

FIG. 4B shows a first series of width modulate pulses 520A of the first bandpass audiosignal 510A of the first channel for high frequency stimulation of the cochlea so as to maintain phase of the audio signal as in FIG. 4A. The pulses may correspond to a synchronous time base of 10 us between the leading edge of each pulse. The width of the pulses can vary based on the amplitude of the first bandpass filtered audio signal 510A. The corresponding frequency of the pulses is about 100 kHz and the pulses are demodulated by the cochlea with cochlear low pass filtering such that the user perceives sound with phase of the sound maintained and such that the user can perceive sound localization cues.

The bandpass filtered signals of the other channels can be processed similarly with cochlear low pass filtering of the high frequency signal such that the user perceives sound with phase of the sound maintained for each of the channels and such that the user can perceive sound localization cues from the combined channels.

While the pulse width modulated light pulses can be generated in many ways, the speech processor may comprise digital bandpass filters to output the bandpass filtered signal as an array for each channel, and the pulse width modulation circuitry can determine a width of each pulse of each channel based on the output, for example. As the output of the pulse width modulation circuitry can be digital and stored in the random access memory of the processor, the pulses to the light source can be delivered so as to maintain substantially the amplitude and phase of the output pulse modulation signal. For example, the timing and/or phase of the pulses of the signal can be maintained to within about 100 us for a 10 kHz pulse width modulation signal, and within about 10 us for a 100 kHz. Although the serial output among the channels may be used as described above and the timing and/or phase of each of the pulses of the channels may be shifted slightly relative to each other, the timing and/or phase of the corresponding pulses among the channels is substantially maintained with the serial output. For example, the corresponding light pulses of the serial output among the channels can be maintained to within about 100 us, for example within about 50 us, within about 20 us, or within about 10 us. The number of channels may comprise 2 channels, 4 channels, 8 channels, 16 channels, 32 channels or more for example. The frequency of the light pulses of each channel can be above at least about 10 kHz, for example 20 kHz, 40 kHz, 80 kHz, for example. The channels may be combined having the frequency of the light pulses of each channel as described above, such that the frequency of the width modulated pulses of the multiplexed optical signal transmitted across the eardrum may comprise, 40 kHz, 160 kHz, 640 kHz, 1280 kHz, or more, for example. Based on the teachings described herein, a person of ordinary skill in the art can determine the number of channels and the timing and/or phase of the pulses to maintain the phase of the audio signal when the cochlea is stimulated, for example so as to provide sound localization cues and so as to inhibit distortion.

EXPERIMENTAL

Based on the teachings described herein, a person of ordinary skill in the art can conduct experiments to determine empirically the amount of light energy to stimulate tissue. For example, one or more optical fibers can be inserted into the cochlea to stimulate nerve tissue, and the depth of insertion, pulse intensity, duration and wavelength to stimulate tissue determined. The optical array, light source(s) and multiplexer can be constructed so as to stimulate tissue with light, for example to stimulate nerve tissue of the cochlea to transmit sound to a user. The experiment described below is an example of such an experiment that has been performed.

Human Eardrum Transmission Experiment

The below described experiment was conducted to measure transmission of infrared light through the eardrum and determine arrangements of the input assembly 20 and output assembly 30.

Objective: To determine the amount of light transmission loss through a human eardrum at posterior, inferior and anterior positions and the amount of scatter by the eardrum.

Figure 5:
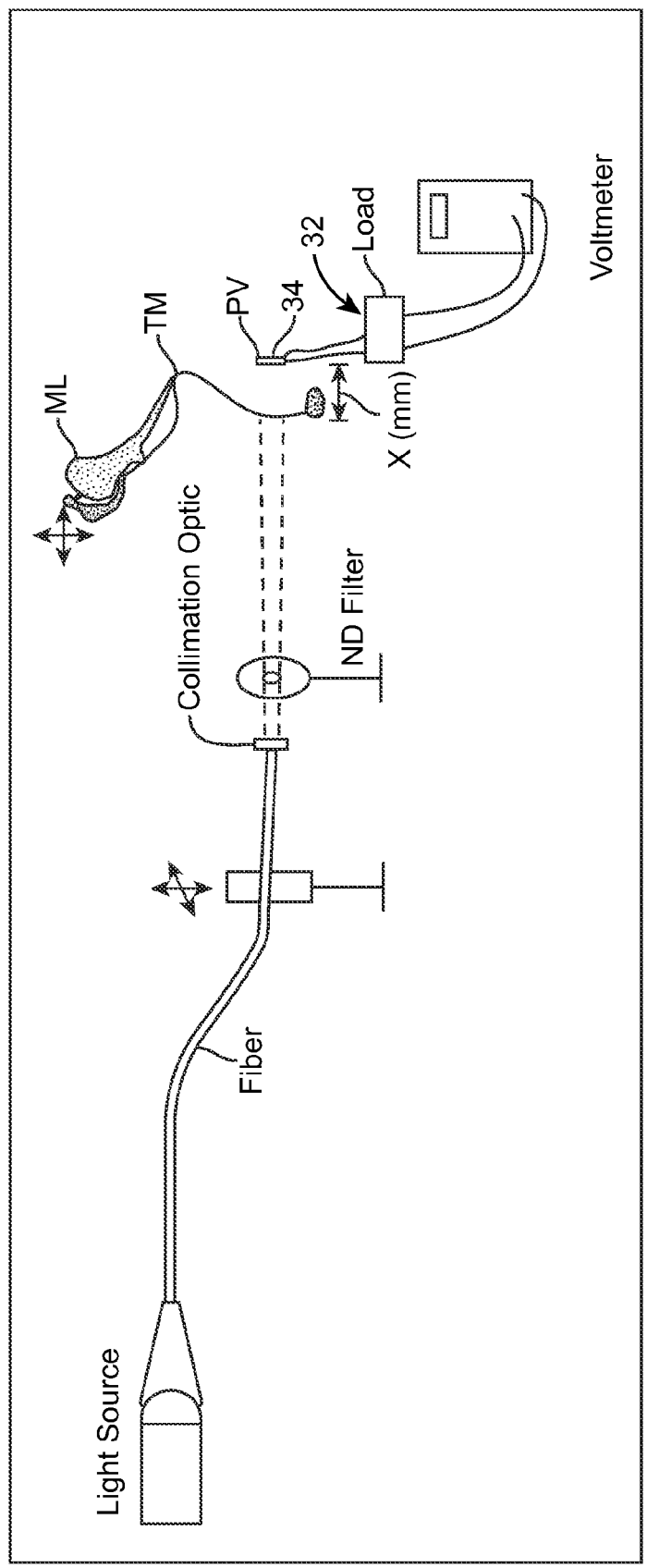
FIG. 5 shows an experimental set up to determine optical transmission through the tympanic membrane, in accordance with embodiments.

Procedure:

FIG. 5 shows the experimental set up to determine optical transmission through the tympanic membrane, in accordance with embodiments. A fiber optic coupled laser diode light source was aligned with a photodiode optical detector. An eardrum was placed in line and the change in optical output from the photodiode determined. The eardrum is mounted to a x,y,z translation stage which allows a change to different positions of the eardrum that the light goes through.

Materials:

Light source—1480 nm laser diode coupled to an optical fiber (250 um diameter, 80 um core);

PhotoDiode—1480 nm photodiode (5.5 mm2);

Load—RLC electrical circuit equivalent to that of a balanced armature transducer coupled to a diaphragm, which can be suitable for determining transmission through the eardrum.

Collimation optics and a Neutral Density Filter (NE20B);

DC Voltmeter (Fluke 8060A);

Translation stages; and

Human cadaver eardrum with attached malleus (incus and other medial components removed)

Results

No Tympanic Membrane

The current was set such that the photodiode was in the saturation region. A neutral density (ND) filter was used to attenuate the light output to reduced the PD response. The measurements indicate that the ND filter attenuated the light source by 20.5 dB. This ensured that all measurements reported are from the linear region.

The photodiode voltage in response to the collimated light beam without the eardrum was measured at the beginning of the measurements and at the end of experiment. The difference was less than 1%.

With no TM and ND filter, the output in mV was 349. With the ND filer and no TM, this output decreased to within a range from about 32.9 to 33.1, corresponding to a linear change of 0.095 and −20.5 dB.

With Tympanic Membrane

Measurements were made at anterior, inferior, and posterior positions of the eardrum. The eardrum was moved at different locations relative to the photodiode and it's distance X (in mm) approximated. Table 1 shows the measured voltages corresponding to the different positions and different eardrum locations.

TABLE 1

| | Measured photodiode voltages corresponding to transmission loss from the eardrum | | | | |
|---|---|---|---|---|---|
| x (mm) | 0.1 | 0.5 | 1 | 2 | 3 |
| Posterior | 28 mV | 26.6 mV | 25.4 mV | 23.4 mV | 20.6 mV |
| Inferior | | | 23.6 mV | 21.1 mV | 17.1 mV |
| Anterior | | | 21.4 mV | 20.2 mV | 18.2 mV |

The posterior placement shows the highest voltage for all distances and has values of 28, 26.6, 25.4 23.4 and 20.6 for distances of 0.1, 0.5, 1, 2 and 3 mm, respectively.

For each eardrum position and location, the optical fiber was adjusted to maximize the PD voltage. This ensured that the light beam was maximally on the photodiode surface and that the measured response was due to transmission loss and not due to misalignments.

Calculations

The measured voltages were converted to percent transmission loss (hereinafter "TL") as follows:

$$\%TL = ((V_{NoTM} - V_{WithTM})/V_{NoTM}) * 100$$

where $V_{NoTM}$ is the measured voltage with no tympanic membrane and $V_{WithTM}$ is the measured voltage with the tympanic membrane Table 2 below shows the calculated % Transmission Loss using the above equation.

TABLE 2

| | % Transmission loss | | | | |
|---|---|---|---|---|---|
| x (mm) | 0.1 | 0.5 | 1 | 2 | 3 |
| Posterior | 16 | 20 | 23 | 29 | 38 |
| Inferior | | | 29 | 36 | 48 |
| Anterior | | | 35 | 39 | 45 |
| Average | | | 29 | 35 | 44 |

At all locations the posterior placement showed the least transmission loss and values of 16, 20, 23, 29 and 38% at distances of 0.1, 0.5, 1, 2 and 3 mm, respectively.

With the PD very close to the eardrum (within about 0.1 mm), the TL is about 16%. The TL could only be measured for the Posterior position.

Of the three positions of the eardrum, the posterior position is better than the inferior position by 6-10%, and better than the anterior position by 7-12%.

As the eardrum is moved away from the PD, the transmission loss increases linearly for all three positions. The average transmission loss is about 29%, 35%, and 44% averaged across the three different positions for the 1, 2 and 3 mm locations respectively.

Experimental Conclusions

The transmission loss due to the eardrum is lowest at the posterior position (16%). The loss increases as the photodiode is moved away from the eardrum due to scatter of the collimated beam by the eardrum. At 3 mm from the eardrum, the average loss was as much as 44%. These data shown the unexpected result that there is more loss due to light scatter at angles away from the detector surface induced by the eardrum than due to transmission of light through the eardrum, and the detector and coupler such as a lens can be shaped appropriately so as to collect transmitted light scattered by the eardrum. These data also show the unexpected result that light transmission is higher through the posterior portion of the eardrum.

As the eardrum can move, the detector in a living person should be at least about 0.5 mm from the eardrum. The data suggest that a detector and/or component such as a lens can be shaped to fit the eardrum and provide improved transmission, for example shape with one or more of an inclined surface, a curved surface, and can be positioned within a range from about 0.5 mm to about 2 mm, for example.

The above data shows that illuminating a portion of the eardrum and placing a detector near the illuminated portion, for example can achieve transmission coupling efficiency between the projected light beam and detector of a least about 50% (corresponding to 50% loss), for example at least about 60% (corresponding to 40% loss). With posterior placement of the detector and illumination of a portion of the posterior region of the eardrum, the coupling efficiency can be at least about 70%, for example 80% or more. These unexpectedly high results for coupling efficiency indicate that illumination of a portion of the eardrum and a detector sized to the illuminated portion can provide efficiencies of at least about 50%. Also, the unexpected substantially lower transmission loss for the posterior portion of the eardrum as compared to each of the inferior and anterior portions indicates that transmission can be unexpectedly improved with posterior placement when most of the eardrum is illuminated. For example, the transmission coupling efficiency of the optical fiber to the photodetector can be improved substantially when the photodetector is positioned in the posterior portion of the middle ear cavity, for example the inferior posterior portion of the middle ear cavity, and an optical fiber is positioned in the ear canal without collimation optics such that light is emitted directly into the ear canal from the end of the optical fiber. Also, the high amount of light transmission through the eardrum shows that the optically multiplexed light can be transmitted through the eardrum, and that the channels of sound encoded with the optically multiplexed signal transmitted through the eardrum can stimulate channels of the cochlea.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims and the full scope of the equivalents thereof.

What is claimed is:

1. A method of stimulating tissue, the method comprising: transmitting multiplexed light energy to the tissue to stimulate the tissue with the multiplexed light energy, wherein the multiplexed light energy is transmitted through an eardrum, and wherein the eardrum acts as a transmission medium for the transmitted multiplexed light energy.

2. A method of transmitting a sound to a user having an eardrum, the user having a cochlea comprising a tissue, the method comprising: transmitting a multiplexed optical signal to the tissue of the cochlea such that the user hears the sound in response to the multiplexed optical signal and wherein the multiplexed optical signal is transmitted through the eardrum, and wherein the eardrum acts as a transmission medium for the transmitted multiplexed optical signal.

3. The method of claim 2 wherein the multiplexed optical signal is transmitted to an optical structure supported with the middle ear, the optical structure configured to separate wavelengths of the multiplexed signal to stimulate the cochlea.

4. The method of claim 3 wherein the optical structure is affixed to the middle ear.

5. The method of claim 3 wherein the optical structure is sized to pass through an incision in the eardrum for placement in the middle ear.

6. The method of claim 3 wherein the optical structure comprises at least one of an optical filter, an optical fiber, a grating, an etalon, a plurality of optical fibers, a waveguide, a plurality of waveguides, a mirror or a prism.

7. The method of claim 3 wherein the multiplexed optical signal comprises a plurality of channels, each channel of the plurality corresponding to at least one frequency of the sound.

8. The method of claim 7 wherein the plurality of channels corresponds to at least about sixteen channels and said at least one frequency corresponds to at least about sixteen frequencies.

9. The method of claim 7 wherein the multiplexed optical signal is transmitted through the eardrum with a plurality of light sources, each light source configured to transmit a light signal corresponding to said channel of the plurality such that said light source corresponds to said at least one frequency of sound.

10. The method of claim 9 wherein the plurality of light sources comprises at least three light sources and wherein each of the at least three light sources is configured to emit separate wavelengths of light.

11. The method of claim 2 wherein the multiplexed optical signal is transmitted through the eardrum of the user to at least one optical waveguide, the at least one optical waveguide affixed to the middle ear and coupled to an optical array positioned at least partially within the cochlea.

12. The method of claim 11 wherein the at least one waveguide comprises at least one optical fiber and the optical array comprises an array of openings configured to emit light from the at least one optical fiber.

13. The method of claim 11 wherein the at least one waveguide and optical array are sized to pass through an incision in the eardrum.

14. The method of claim 11 wherein the multiplexed optical signal comprises a wavelength multiplexed optical signal, the wavelength multiplexed optical signal comprising a plurality of wavelengths such that each wavelength corresponds to an opening of the array.

15. The method of claim 14 wherein each wavelength of the plurality corresponds to an opening of the array.

16. The method of claim 14 wherein the at least one waveguide comprises a plurality of waveguides, each waveguide of the plurality coupled to a corresponding opening of the array and a corresponding wavelength of the plurality of wavelengths such that tissue stimulating light is passed through the opening in response to the wavelength.

17. The method of claim 16 further comprising positioning an optical structure in the middle ear of the user to separate the wavelengths to correspond with each waveguide, and such that each separated wavelength corresponding to each waveguide is transmitted to said each waveguide based on the wavelength.

18. The method of claim 16 further comprising a plurality of optical filters positioned in the middle ear of the user and wherein the wavelengths are separated with the optical filters, each optical filter positioned over one waveguide and configured to pass the wavelengths corresponding to the opening coupled to said one waveguide.

19. The method of claim 16 further comprising a grating configured to select the wavelengths of each waveguide to correspond to each opening.

20. The method of claim 11 wherein the multiplexed optical signal comprise a time division multiplexed signal.

21. The method of claim 20 wherein the time division multiplexed signal comprises a plurality of time-slots, each time slot of the plurality corresponding to an opening of the array.

22. The method of claim 21 wherein the time division multiplexed signal comprises a plurality of time slots and a clock signal and wherein circuitry is coupled to the at least one waveguide and the optical array to receive the clock signal and divide the time division multiplexed signal among the openings of the array such that each time slot corresponds to an opening of the array.

23. The method of claim 22 wherein each time slot corresponds to at least one frequency of the sound such that light is passed through each opening in response to a portion of the multiplexed signal corresponding to the time slot.

24. The method of claim 23 the time division multiplexed signal is pulse width modulated such that each timeslot of the plurality comprises a pulse of light having a duration that corresponds to light through the opening corresponding to said timeslot.

25. The method of claim 20 further comprising a light source positioned in the middle ear and coupled to the optical array positioned at least partially within the cochlea and wherein the light sources emits light in response to the time division multiplexed optical signal.

26. The method of claim 25 further comprising modulator coupled to the light source and wherein the modulator adjusts the light beam to emit light from an opening of the at least one optical fiber in response to the time division multiplexed optical signal.

27. The method of claim 26 wherein the at least one optical waveguide comprises a plurality of wavelength selective optical waveguides and wherein the modulator adjusts a wavelength of the light to direct the light substantially along each of the wavelength selective optical waveguides to an opening on a distal end of said waveguide.

28. The method of claim 26 wherein the light source comprises a laser and the opening comprises a plurality of openings disposed along the at least one waveguide and wherein the modulator is configured to adjust a mode structure of the laser to transmit light selectively through each of the plurality of openings.

29. The method of claim 28 wherein the mode structure comprises a first mode structure and a second mode structure and the plurality of openings comprises a first opening and a second opening and wherein the at least one waveguide is configured to emit light substantially through the first opening in response to the first mode structure and through the second opening in response to the second mode structure.

30. The method of claim 2 wherein the multiplexed optical signal is transmitted to at least one optical fiber extending into the cochlea.

31. The method of claim 30 wherein the at least one optical fiber is sized to pass through an incision in the middle ear.

32. The method of claim 30 wherein the at least one optical fiber comprises a plurality of optical fibers extending into the cochlea, each fiber corresponding to at least one frequency of the sound.

33. The method of claim 30 wherein each fiber is configured to stimulate the cochlea at a predetermined location of the cochlea corresponding to a corresponding range of frequencies in response to the at least one frequency of the sound.

34. The method of claim 2 wherein the multiplexed optical signal is transmitted through at least one of an opening or a window in the eardrum.

35. The method of claim 2 wherein the optical array, the at least one waveguide, and the demultiplexer comprise substantially non-magnetic materials configured for MRI imaging when implanted in the user.

36. A system to stimulate tissue of a user having an eardrum and a middle ear, the system comprising:
  a plurality of openings configured for placement at least partially within the tissue;
  circuitry configured to receive a signal from a source;
  a least one light source coupled to the circuitry and configured to emit a multiplexed optical signal comprising a plurality of light pulses; and
  at least one waveguide configured to receive the multiplexed optical signal and pass light through the openings in response to the light pulses to stimulate the tissue;
  wherein the multiplexed optical signal is transmitted through the eardrum of the user to the at least one waveguide, the at least one waveguide affixed to the middle ear to receive the multiplexed optical signal transmitted through the eardrum, wherein the eardrum acts as a transmission medium for the multiplexed optical signal.

37. A system to transmit an audio signal to a user having an eardrum and a middle ear, the system comprising:
  an optical array comprising a plurality of openings configured for placement at least partially within a cochlea of the user;
  circuitry configured to receive the audio signal from a sound source;
  at least one light source coupled to the circuitry and configured to emit a multiplexed optical signal comprising a plurality of light pulses; and
  at least one waveguide configured to receive the multiplexed optical signal and pass light through the openings in response to the light pulses;
  wherein the multiplexed optical signal is transmitted through the eardrum of the user to the at least one waveguide, the at least one waveguide affixed to the middle ear and coupled to the optical array positioned at least partially within the cochlea, and
  wherein the eardrum acts as a transmission medium for the multiplexed optical signal.

38. The system of claim 37 the circuitry is configured to determine widths of a plurality of light pulses and wherein each light pulse corresponds to an opening of the array and a width of said each light pulse corresponds to an amount of light through said corresponding opening of the array.

39. The system of claim 37 wherein the circuitry is configured to determine frequencies of the audio signal and wherein the frequencies correspond to openings of the array and wherein the circuitry is configured to determine a width of each pulse in response to one or more of the frequencies.

40. The system of claim 37 wherein the at least one light source comprises a plurality of light sources and wherein each light source corresponds to one opening of the array.

41. The system of claim 40 each of the plurality of light sources is configured to emit light comprising wavelengths substantially separated from wavelengths of other light sources of the plurality.

42. The system of claim 40 wherein the plurality of light sources comprises at least three light sources and the optical array comprises at least three openings and wherein each of the at least three light sources corresponds to one opening of the at least three openings of the array.

43. The system of claim 42 each of the at least three light sources is configured to emit light comprising wavelengths substantially separated from others of the at least three light sources and wherein the wavelengths of each source correspond to one opening of the at least three openings.

44. The system of claim 37 wherein the at least one waveguide comprises a plurality of waveguides and wherein each waveguide of the plurality corresponds to one opening of the array.

45. The system of claim 44 wherein the plurality of light waveguides comprises at least three light waveguides and the optical array comprises at least three openings and wherein each of the at least three light waveguides corresponds to one opening of the at least three openings of the array.

46. The system of claim 37 further comprising an optical structure configured to receive the multiplexed optical signal, the optical structure configured for placement in the middle, the optical structure configured to select wavelengths of the multiplexed signal.

47. The system of claim 46 wherein the optical structure is sized to pass through an incision in the eardrum for placement in the middle ear and wherein the optical array is sized for placement at least partially inside the cochlea through a round window of the cochlea.

48. The system of claim 46 wherein the optical structure comprises at least one of an optical filter, a grating, an etalon, a plurality of optical fibers, or a prism.

49. The system of claim 46 wherein the multiplexed optical signal comprises a plurality of optical channels, each optical channel of the plurality corresponding to at least one frequency of the sound.

50. The system of claim 49 wherein the plurality of optical channels corresponds to at least about sixteen channels and said at least one frequency corresponds to at least about sixteen frequencies.

51. The system of claim 49 further comprising an elongate optical transmission structure configured for placement at least partially within the ear canal of the user and wherein the elongate optical transmission structure is configured to transmit multiplexed optical signal through the eardrum.

52. The system of claim 37 wherein the at least one waveguide and the optical array are sized to pass through an incision in the eardrum.

53. The system of claim 37 wherein the multiplexed optical signal comprises a wavelength multiplexed optical signal, the wavelength multiplexed optical signal comprising a plurality of wavelengths such that each wavelength corresponds to an opening of the array.

54. The system of claim 53 wherein each wavelength of the plurality corresponds to an opening of the array.

55. The system of claim 53 wherein the plurality of wavelengths comprises at least three wavelengths and wherein the plurality of openings comprises at least three openings and wherein each wavelength of the plurality corresponds to one opening of the at least three openings.

56. The system of claim 37 wherein the circuitry is configured to transmit a series of the light pulses to correspond to openings of the array.

57. The system of claim 56 wherein the series comprises a plurality of pulses and wherein each pulse of the plurality corresponds to one opening of the plurality of openings.

58. The system of claim 57 wherein the plurality of openings comprises at least three openings and wherein the series comprises at least three pulses and wherein each pulse of the at least three pulses corresponds to one opening of the at least three openings.

59. The system of claim 56 wherein the series comprises a timing pulse.

60. The system of claim 59 wherein the timing pulse comprises a substantially fixed width and wherein the timing pulse comprises energy to power circuitry coupled to the plurality of openings.

61. The system of claim 59 further comprising switching circuitry coupled to the at least one waveguide to couple sequentially each opening of the plurality to the at least one waveguide in response to the timing pulse such that each pulse of the series corresponds to one opening of the plurality.

62. The system of claim 61 wherein the series of pulses comprises a pre-determined order and timing of the pulses and wherein the switching circuitry comprises a timer coupled to switches to open the switches and close the to correspond with pulses of the series.

63. The system of claim 61 wherein the series comprises at least three pulses and wherein the switching circuitry is configured to coupled at least one waveguide sequentially to each opening of the at least three such that each pulse of the series corresponds to one opening of the plurality.

64. The system of claim 56 further comprising a light source positioned in the middle ear and coupled to the optical array positioned at least partially within the cochlea and wherein the light source emits light in response to the time division multiplexed optical signal.

65. The system of claim 64 further comprising modulator coupled to the light source and wherein the modulator adjusts the light beam to emit light from an opening of the at least one optical fiber in response to the time division multiplexed optical signal.

66. The system of claim 65 wherein the at least one optical waveguide comprises a plurality of wavelength selective optical waveguides and wherein the modulator adjusts a wavelength of the light to direct the light substantially along one of the wavelength selective optical waveguides to an opening on a distal end of the waveguide.

67. The system of claim 65 wherein the light source comprises a laser and the opening comprises a plurality of openings disposed along the at least one waveguide and wherein the modulator is configured to adjust a mode structure of the laser to transmit light substantially through one of the plurality of openings.

68. The system of claim 37 wherein the optical array, the at least one waveguide, and the demultiplexer comprise substantially non-magnetic materials configured for MRI imaging when implanted in the user.

69. A method of providing a hearing prosthesis for a user, the method comprising:
  making an incision in an eardrum of the user, the eardrum comprising an annulus; and
  passing an optical array, at least one waveguide, and a demultiplexer through the incision;

wherein the demultiplexer is placed to receive multiplexed light energy transmitted through the eardrum, and wherein the eardrum acts as a transmission medium for the multiplexed optical signal.

70. The method of claim 69 wherein the incision extends at least partially through the annulus.

71. The method of claim 69 wherein the eardrum is positioned to a side of an ear canal to pass the optical array, the demultiplexer and the at least one waveguide through the incision.

72. The method of claim 69 wherein the at least one waveguide and the demultiplexer are affixed to the middle ear of the user.

73. The method of claim 69 wherein the optical array is positioned at least partially through a round window and wherein the at least one waveguide and the demultiplexer are positioned in a middle ear of the user.

74. The method of claim 73 wherein the at least one waveguide and the demultiplexer are affixed to the middle ear of the user.

75. The method of claim 69 wherein the at least one waveguide comprises at least three waveguides.

76. The method of claim 75 wherein the demultiplexer comprises an optical demultiplexer.

77. The method of claim 76 wherein the optical demultiplexer comprises at least three filters to separate at least three wavelengths of light.

78. The method of claim 69 wherein the demultiplexer comprises switching circuitry and a timer.

79. The method of claim 69 wherein the optical array, the at least one photodetector, and the demultiplexer passed through the incision comprise substantially non-magnetic materials configured for MRI imaging.

80. A device to stimulate tissue of a user having an eardrum, the device comprising:

means for generating a multiplexed optical signal;

means for transmitting the multiplexed optical signal through the eardrum, wherein the eardrum acts as a transmission medium for the transmitted multiplexed optical signal, and means for stimulating tissue in response to the optical signal.

* * * * *